US006495131B1

(12) United States Patent
Draijer-van der Kaaden et al.

(10) Patent No.: US 6,495,131 B1
(45) Date of Patent: Dec. 17, 2002

(54) INTERLEUKIN-3 GENE THERAPY FOR CANCER

(75) Inventors: Marie Elisabeth Draijer-van der Kaaden, Leiden; Abraham Bout, Moerkapelle; Dirk Willem van Bekkum, Rotterdam, all of (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 09/481,201

(22) Filed: Jan. 11, 2000

Related U.S. Application Data

(63) Continuation of application No. PCT/NL98/00406, filed on Jul. 13, 1998.

(51) Int. Cl.[7] .................. A01N 63/00; A01N 43/04; C07H 21/02; C07H 21/04; C12N 5/00; C12N 15/00; C12N 15/63

(52) U.S. Cl. .................. 424/93.2; 514/44; 536/23.5; 536/23.1; 435/320.1; 435/325; 435/455

(58) Field of Search .................. 514/44; 536/23.1, 536/23.5; 435/320.1, 325, 69.1, 455; 424/93.2, 93.1, 93.6

(56) References Cited

U.S. PATENT DOCUMENTS 5,069,662 A * 12/1991 Bodden .................. 604/4

OTHER PUBLICATIONS

Anderson WF, Nature 392:25–30, 1998.*
Verma et al Nature 389:239–242, 1997.*
Touchette, Nat. Med. 2(1) 7–8, 1996.*
Kay et al, PNAS 94:12744–12746, 1997.*
Blu et al N Engl J Med. 333(18):1204–7 1995.*
Kelloff et al, Eur. J. Cancer. 35(14):2031–2035, 1999.*
Gomez–Navarro et al, Eur. J. Cancer. 35(6);867–885, 1999.*
Mastrangelo et al, Semin. in Oncology. 23(1):4–21, 1996.*
de Vries et al, Stem Cells 11(2):72–80, 1993, 1998.*
Lingam et al., A single centre's 10 year experience with isolated limb perfusion in the treatment of recurrent malignant melanoma of the limb, 1996, European Journal of Cancer, vol. 32A, pp. 1668–1673.*
Esandi et al., Cytokine gene therapy for experimental non small cell lung cancer (NSCLC), 1996, Cancer Gene Therapy, vol. 3 No. 6.*
Esandi et al., "Cytokine gene therapy for experimental non small cell lung cancer (NSCLC)", XP 002050015, 1 page.
Henon et al., "Mobilization of peripheral blood stem cells with cehmotherapy and cytokines in multiple myeloma", XP 002050018, Aug. 1995, 1 page.
Hill et al., "Use of the carbon dioxide laser to manage cutaneous metastases from malignnant melanoma", *British Journal of Surgery*, 1996, 83, pp. 509–512.
PCT/NL98/00406 International Preliminary Examination Report, Oct. 15, 1999, 6 pages.
Shibata et al., "Interleukin 3 Perfusion Prevents Death Due to Acute Anemia Induced by Monoclonal Antierythrocyte Autoantibody", *J. Exp. Med.*, vol. 171, May 1990, pp. 18–09–1814.

* cited by examiner

Primary Examiner—Scott D. Priebe
Assistant Examiner—Sumesh H Kaushal
(74) Attorney, Agent, or Firm—TraskBritt

(57) ABSTRACT

Means and methods for treating tumors in a mammal, in particular, malignant solid tumors, using adenovirus derived material and interleukin-3 ("IL-3 "). Tthe adenovirus derived material preferably encodes IL-3 activity. Such an adenovirus is preferably administered systemically to the mammal, optionally in an isolated perfusion setting. In preferred embodiments, IL-3 activity is combined with other cytotoxic activity.

13 Claims, 18 Drawing Sheets

FIG. 17A

Figure 1:
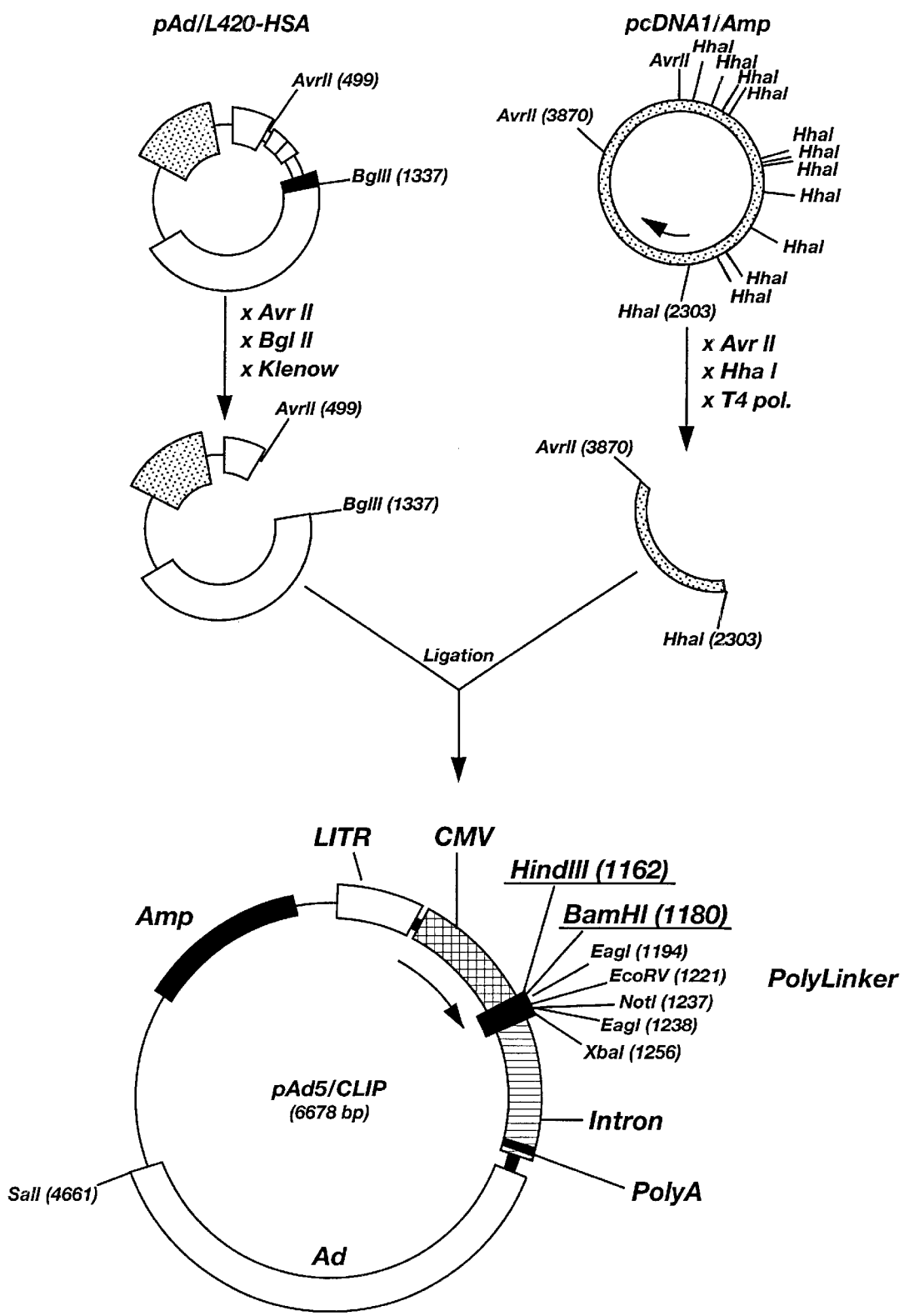

| Conc. hIL-3 (pg/ml) | Abs$_{450nm}$ |
|---|---|
| Standard curve: | |
| 0 | 0.007 |
| 31.25 | 0.017 |
| 62.5 | 0.024 |
| 125 | 0.044 |
| 250 | 0.077 |
| 500 | 0.154 |
| 1000 | 0.298 |
| 2000 | 0.518 |
| Sample | |
| Plaque-3 | 0.541 |

FIG. 17B

| Standard curve: | |
|---|---|
| conc. hIL-3 (ng/ml) | Abs$_{490nm}$ |
| 80 | 0.921 |
| 40 | 0.782 |
| 20 | 0.684 |
| 10 | 0.576 |
| 5 | 0.593 |
| 2.5 | 0.455 |
| 1.25 | 0.432 |
| 0.625 | 0.424 |
| 0.3125 | 0.409 |
| 0.1563 | 0.412 |
| 0.0781 | 0.399 |
| 0.0391 | 0.417 |
| 0.0195 | 0.412 |
| 0.0098 | 0.432 |

| Sample dilution curve: | |
|---|---|
| dilution factor | Abs$_{490nm}$ |
| 1 | 0.989 |
| 2 | 0.914 |
| 4 | 0.769 |
| 8 | 0.618 |
| 16 | 0.565 |
| 32 | 0.492 |
| 64 | 0.470 |
| 128 | 0.401 |
| 256 | 0.389 |
| 512 | 0.403 |
| 1024 | 0.409 |
| 2048 | 0.410 |
| 4096 | 0.390 |
| 8192 | 0.410 |

SEQUENCE LISTING

<160> NUMBER OF SEQ ID NOS: 10

<210> SEQ ID NO 1
<211> LENGTH: 27
<212> TYPE: DNA
<213> ORGANISM: Unknown Organism
<220> FEATURE:
<223> OTHER INFORMATION: Description of Unknown Organism:PRIMER SV40-1

<400> SEQUENCE: 1
gggggatccg aacttgttta ttgcagc                              27

<210> SEQ ID NO 2
<211> LENGTH: 25
<212> TYPE: DNA
<213> ORGANISM: Unknown Organism
<220> FEATURE:
<223> OTHER INFORMATION: Description of Unknown Organism:PRIMER SV40-2

<400> SEQUENCE: 2
gggagatcta gacatgataa gatac                                25

<210> SEQ ID NO 3
<211> LENGTH: 27

```
<212> TYPE: DNA
<213> ORGANISM: Unknown Organism
<220> FEATURE:
<223> OTHER INFORMATION: Description of Unknown Organism:PRIMER AD5-1

<400> SEQUENCE: 3
gggagatctg tactgaaatg tgtgggc                                          27

<210> SEQ ID NO 4
<211> LENGTH: 24
<212> TYPE: DNA
<213> ORGANISM: Unknown Organism
<220> FEATURE:
<223> OTHER INFORMATION: Description of Unknown Organism:PRIMER AD5-2

<400> SEQUENCE: 4
ggaggctgca gtctccaacg gcgt                                             24

<210> SEQ ID NO 5
<211> LENGTH: 47
<212> TYPE: DNA
<213> ORGANISM: Unknown Organism
<220> FEATURE:
<223> OTHER INFORMATION: Description of Unknown Organism:PRIMER LTR-1

<400> SEQUENCE: 5
ctgtacgtac cagtgcactg gcctaggcat ggaaaaatac ataactg                    47

<210> SEQ ID NO 6
<211> LENGTH: 64
<212> TYPE: DNA
<213> ORGANISM: Unknown Organism
<220> FEATURE:
<223> OTHER INFORMATION: Description of Unknown Organism:PRIMER LTR-2

<400> SEQUENCE: 6
gcggatcctt cgaaccatgg taagcttggt accgctagcg ttaaccgggc gactcagtca      60
atcg                                                                  64

<210> SEQ ID NO 7
<211> LENGTH: 28
<212> TYPE: DNA
<213> ORGANISM: Unknown Organism
<220> FEATURE:
<223> OTHER INFORMATION: Description of Unknown Organism:PRIMER HSA1

<400> SEQUENCE: 7
gcgccaccat gggcagagcg atggtggc                                         28

<210> SEQ ID NO 8
<211> LENGTH: 50
<212> TYPE: DNA
<213> ORGANISM: Unknown Organism
<220> FEATURE:
<223> OTHER INFORMATION: Description of Unknown Organism:PRIMER HSA2

<400> SEQUENCE: 8
gttagatcta agcttgtcga catcgatcta ctaacagtag agatgtagaa                 50

<210> SEQ ID NO 9
<211> LENGTH: 34
<212> TYPE: DNA
<213> ORGANISM: Unknown Organism
<220> FEATURE:
<223> OTHER INFORMATION: Description of Unknown Organism:PRIMER
      huIL3-forward
```

-continued

```
<400> SEQUENCE: 9
ccccaagctt gccaccatga gccgcctgcc cgtc                                34

<210> SEQ ID NO 10
<211> LENGTH: 26
<212> TYPE: DNA
<213> ORGANISM: Unknown Organism
<220> FEATURE:
<223> OTHER INFORMATION: Description of Unknown Organism:PRIMER
      hu-IL3-reverse

<400> SEQUENCE: 10
gcgggatcct caaaagatcg cgaggc                                         26
```

| | |

INTERLEUKIN-3 GENE THERAPY FOR CANCER

CROSS REFERENCE TO RELATED APPLICATION

This application is a continuation of pending International Application No. PCT/NL98/00406, filed Jul. 13, 1998 designating the United States of America, which itself claims priority from EP972167.9 filed Jul. 11, 1997, the contents of both of which are incorporated by this reference.

The present invention lies in the field of anti-cancer (gene) therapy. In particular, the invention relates to selective killing of (solid) tumor cells in a mammal by gene delivery via the blood circulation.

Many different kinds of solid tumors occur in the body of mammals, including humans. In many cases these tumors are extremely difficult to treat, especially in advanced cancer with metastases. Currently available therapies include surgery, radiation therapy, chemotherapy, radio-immunotherapy, cytokine treatment and hyperthermia. All these therapies have important limitations and disadvantages. E.g., surgery can only be performed on localized, accessible tumors; radiation and chemotherapy are associated with both acute and latent toxicity, and responses are often limited; radio-immunotherapy and hyperthermia have limited application and effectivity; and cytokine administration is often associated with toxicity and evokes many pleiotropic side-effects. Often said therapies are combined to improve efficacy and to decrease toxic side-effects. However, in general, the effectivity of said therapies and their combinations is still unsatisfactory.

More recently, gene therapy has been proposed as a novel approach to treat malignancies. The concept of gene therapy comprises the introduction of a molecule carrying genetic information into cells of a host, whereby said genetic information has a functional format. Said genetic information may comprise a nucleic acid molecule that encodes a protein. In this case said functional format means that the protein can be expressed by the machinery of the host cell. The genetic information may also comprise or encode nucleic acid molecules with a sequence that is complementary to that of a nucleic acid molecule present in the host cell. The functional format in this case is that the introduced nucleic acid molecule or copies made thereof in situ are capable of base pairing with the complementary nucleic acid molecule present in the host cell. Said genetic information may furthermore comprise a nucleic acid molecule that encodes or is itself a so-called ribozyme or deoxyribozyme. In this case said functional format means that said nucleic acid molecule or copies made thereof in situ are capable of specifically cleaving a nucleic acid molecule present in the host cell. Said genetic information may furthermore comprise a nucleic acid molecule that encodes or is itself a so-called decoy molecule. In this case said functional format means that said nucleic acid molecule or copies made thereof in situ (nucleic acid molecules or proteins) are capable of specifically binding a peptide molecule present in the host cell.

Said introduction of a molecule carrying genetic information into cells of a host is achieved by various methods known in the art. Said methods include, but are not limited to, direct injection of naked DNA constructs, bombardment with gold particles loaded with said constructs, and macromolecule mediated gene transfer using, e.g., liposomes, biopolymers, and the like. Preferred methods use gene delivery vehicles derived from viruses, including but not limited to adenoviruses, retroviruses, vaccinia viruses and adeno associated viruses. Because of the much higher efficiency as compared to e.g. vectors derived from retroviruses, vectors derived from adenoviruses (so-called adenoviral vectors) are the preferred gene delivery vehicles for transferring nucleic acid molecules into host cells in vivo.

The adenovirus genome is a linear double-stranded DNA molecule of approximately 36000 base pairs. The adenovirus DNA contains identical Inverted Terminal Repeats (ITR) of approximately 100 base pairs with the exact length depending on the serotype. The viral origins of replication are within the ITRs exactly at the genome ends. Adenoviruses can be rendered replication defective by deletion of the early-region 1 (E1) of their genome. Vectors derived from human adenoviruses (so-called adenoviral vectors), in which at least the E1 region has been deleted and replaced by a gene-of-interest, have been used extensively for gene therapy experiments in both pre-clinical and clinical phase. Apart from replication defective adenoviral vectors, helper independent or replication competent vectors, either or not containing a gene-of-interest, can also be used for gene therapy purposes. Adenoviral vectors have a number of features that make them particularly useful for gene therapy for malignancies. These features include (1) the biology of adenoviruses is characterized in detail, (2) adenoviruses are not associated with severe human pathology, (3) adenoviruses are extremely efficient in introducing their DNA into host cells, (4) adenoviruses can infect a wide variety of cells and have a broad host-range, (5) adenoviral vectors allow insertion of relatively large fragments of foreign DNA, (6) adenoviruses can be produced in large quantities with relative ease, and (7) adenoviral vectors are capable of transferring nucleic acid molecules very efficiently into host cells in vivo (Brody and Crystal, Ann. N. Y. Acad. Sci. 716(1994): 90–101).

The present inventors and their coworkers as well as others have demonstrated that recombinant adenoviral vectors efficiently transfer nucleic acid molecules to the liver of rats (Herz and Gerard, Proc. Natl. Acad. Sci. U.S.A., 96 (1993):2812–2816) and to airway epithelium of rhesus monkeys (Bout et al., Gene Ther., 1 (1994):385–394; Bout et al., Hum. Gene Ther., 5(1994):3–10). In addition, the present inventors, their coworkers and others have observed a very efficient in vivo adenoviral vector mediated gene transfer into a variety of established solid tumors in animal models (lung tumors, glioma) and into human solid tumor xenografts in immune-deficient mice (lung) (Haddada et al., Biochem. Biophys. Res. Comm. 195 (1993):1174–1183; Vincent et al., Hum. Gene Ther., 7 (1996):197–205; reviewed by Blaese et al., Cancer Gene Ther., 2 (1995): 291–297. Thus, preferred methods for in vivo gene transfer into tumor cells of nucleic acid molecules that encode molecules that can be used to kill said tumor cells make use of adenoviral vectors as gene delivery vehicles.

Said molecules that can be used to kill tumor cells include but are not restricted to suicide enzymes that convert a non-toxic prodrug into a toxic compound (e.g. the HSV-tk/ganciclovir system), cytokines, antisense nucleic acid molecules, ribozymes, and tumor suppressor proteins. In addition, treatment of cancer by gene therapy methods also includes the delivery of replicating vectors that are toxic to the tumor cells by themselves.

Gene therapy by introduction of nucleic acid molecules encoding suicide enzymes has been widely tested on a variety of tumor models. Especially the transfer of the Herpes simplex virus thymidine kinase (HSV-tk) gene into tumor cells in conjunction with systemic administration of the non-toxic substrate ganciclovir has proven to be an effective way of killing tumor cells in vivo (Esandi et al., Gene Ther., 4 (1997) :280–287; Vincent et al., J. Neurosurg., 85 (1996) :648–654; Vincent et al., Hum. Gene Ther., 7 (1996) :197–205). An important advantage of the HSV-tk/ganciclovir system is that upon ganciclovir treatment HSV-tk transduced tumor cells mediate a significant killing effect on neighboring untransduced tumor cells, the so-called bystander effect (Culver et al, Science 256 (1992) : 1550–1552). Thus, using this approach there is no absolute need for gene transfer into every individual cell in a solid tumor to achieve successful gene therapy. A limitation of this approach, however, is that the effect remains local. Consequently, the HSV-tk gene needs to be delivered into every individual solid tumor or metastasis throughout the body.

Gene therapy for cancer by the introduction of nucleic acid molecules encoding cytokines is based on the concept of enhancing the immune response against the tumor cells. The ultimate goal of this approach is to obtain regression of the treated tumor and simultaneously induce such a high degree of immunity that coexisting metastases are also destroyed. The mechanism by which the cytokine enhances the immune response against the tumor cells most likely in many cases involves eliciting an inflammatory type cell infiltration that results in improved antigen presentation. During the local inflammation invading cells may lyse the tumor cells, releasing tumor antigens in a form that can be presented by other subpopulations of the invaders to T lymphocytes. These, in their turn could act against coexisting metastases. Compared to administration of a cytokine protein the gene transfer approach has the important advantage of high-level production of the cytokine at the site of the tumor, while systemic concentrations of the cytokine remain low. This avoids any pleiotropic and toxic side effects associated with said cytokine. Signs of (partially) successful cancer treatment have been obtained with tumor cells expressing IL-2 (Fearon et al., Cell 60: 397–401, 1990; Gansbacher et al., J. Exp. Med. 172:1217, 1990), IL-4 (Golumbek et al., Science 254:713–716, 1991; Platzer et al., Eur. J. Immunol. 22:1729–1733, 1992), interferon-gamma (Gansbacher et al., Cancer Res. 50:7820–7824, 1990), interferon-alpha (Ferrantini et al., Cancer Res. 53:1107–1112, 1993), TNF alpha (Blankenstein et al., J. Exp. Med. 173:1047–1052, 1991), IL-7 (Hock et al., J. Exp. Med. 174:1291–1298, 1991; McBride et al., Cancer Res. 52:3931–3937, 1992), G-CSF (Colombo et al., J. Exp. Med. 173:889–897, 1991), GM-CSF (Dranoff et al., Proc. Natl. Acad. Sci. U.S.A. 90:3539–3543, 1993), IL-12 (Tahara et al., Cancer Res. 54:182–189, 1994), IL-1 (Apte et al., In: Cytokine-induced tumor immunogenicity, Acad. Press, London, pp. 97–112, 1994; Apte et al., Folia Biol. Praha 40:1–18, 1994; Douvdevani et al., Int. J. Cancer 51:822–830, 1992; Nakata et al., Cancer Res. 48:584–588, 1988; Zöller et al., Int. J. Cancer 50:443–449, 1992) and IL-3 (McBride et al., Folia Biol. Praha 40:62–73, 1993; Pulaski et al., Cancer Res. 53:2112–2117, 1993). The present inventors and their coworkers have previously observed partial regression of a non-immunogenic solid tumor (L42 non small cell lung cancer; Kal et al., NCI Monographs 6:111–114, 1988; Kal et al., Radiother. Oncol. 6:231–238, 1986; Kal et al., J. Natl. Cancer Inst. 76:943–946, 1986) growing subcutaneously in WAG/Rij rats after intra-tumor injection of adenoviral vectors expressing IL-1a or IL-3. This regression occurred both in the injected tumor and in an untreated distant (contralateral) L42 tumor (patent application EP 96.202725, incorporated herein by reference).

Interleukin-3 (IL-3) is a cytokine well described as a hematopoietic growth factor that has a wide range of target cells including progenitor cells of every lineage, excluding cells committed to the T and B lymphoid lineage (Schrader et al., In: Lymphokines, Acad. Press, San Diego, 1988). The main production of IL-3 by activated T cells has led to the hypothesis that IL-3 is not involved in steady-state hematopoiesis but functions as a link between on one hand the T lymphocytes of the immune system, which sense invasion of the body by foreign materials, and on the other hand the hematopoietic system which generates the cellular elements that mediate defense and repair responses (Ihle, In: Immunoregulatory cytokines and cell growth, Karger, Basel, 1989). IL-3 exerts a broad spectrum of biological properties (Ihle et al ., J. Immunol. 131:282, 1983), including stimulatory activity on several myeloid leukemia cell lines, formation of granulocyte-macrophage colonies, mast cell growth factor activity, P cell-stimulating activity and histamine producing cell-stimulating factor activity. In addition, IL-3 is capable of promoting the proliferation of megakaryocyte colony-forming cells, of supporting the differentiation of eosinophils and pre-B-cell precursors, of supporting proliferation of Natural Cytotoxic (NC) cells but not Natural Killer (NK) cells and of promoting the formation of osteoclasts. IL-3 also stimulates the effector functions of monocytes, eosinophils and basophils, thereby having the potential to regulate inflammation and allergy (Elliott et al., J. Immunol. 145:167, 1990; Haak-Frendesco et al., J. Clin. Invest. 82:17, 1988; Lopez et al., J. Cell. Physiol. 145:69, 1990). Human endothelial cells express the IL-3 receptor which expression is enhanced by tumor necrosis factor alpha (TNF-$\alpha$). IL-3 stimulation of TNF-$\alpha$-activated endothelial cells enhances IL-8 production, E-selectin expression and neutrophil transmigration (Korpelainen et al., Proc. Natl. Acad. Sci. U.S.A. 90:11137, 1993). This suggests that IL-3 plays a role in inflammation not only by stimulating effector functions of mature leukocytes but also by regulating their localization to sites of inflammation through its action on the endothelium.

There are several ways to administer recombinant adenoviral vectors with therapeutic genes into solid tumors that grow in a mammalian animal body. Currently, cancer gene therapy protocols predominantly use direct injection of the recombinant vector into the tumor (e.g., Haddada et al., Biochem. Biophys. Res. Comm. 195:1174–1183, 1993; Vincent et al., Hum. Gene Ther. 7:197–205, 1996). The major disadvantage of this application route is that metastases, and in particular micrometastases, in advanced cancer are practically impossible to reach with this approach. Therefore, such a gene therapy relies solely on a distant (immune mediated) effect of the introduced genetic information. Using current technology, said distant effect may not be expected to be complete and, consequently, may not be expected to cure the disease.

An alternative, and possibly better way of delivering genetic material into solid tumors and/or their metastases could be by administering the recombinant adenovector via the blood or lymphatic circulation. All established tumors, both primary and metastatized, that are larger than a few millimeter in diameter are vascularized (Folkman et al., J. Nat. Cancer Inst. 82:4, 1990; Folkman and Shing, J. Biol. Chem. 267:10931–10934, 1992). In addition, distant metastases usually emerge after migration of tumor cells from the primary tumor through the blood or lymphatic circulation. Thus, all solid tumors are in close contact with the circulation and, in priciple, could be reached via the circulation. Moreover, killing of a solid tumor does not neccessarily depend on gene transfer into the tumor cells themselves. Gene therapy strategies have been proposed where genetic material (e.g., the HSV-tk gene) is introduced into endothelial cells of the tumor vasculature (e.g., WO96/21416). This should result in destruction of the tumor vasculature, ultimately leading to tumor necrosis.

The total capillary surface area in an adult human is approximately 100 m$^2$ comprising approximately $10^{12}$ endothelial cells, whereas the endothelial cell content of the vasculature of a solid tumor is about 4-log less (Chan and Harris, In: The Internet book of Gene Therapy. Cancer Therapeutics, eds. R. E. Sobol and K. J. Scanlon, 1995, Appleton & Lange, CT, pp. 211–227). Based on these estimations, intravascularly administered adenoviral vectors only have a 0.01% chance of interacting with endothelial cells in the vasculature of a distant tumor. The proliferation index of endothelial cells in the vasculature of a tumor is about 100-fold higher than that of normal endothelial cells (Hobson and Denekamp, Br. J. Cancer, 1984, 49:405–413). Thus, if gene delivery would preferentially occur into actively proliferating cells, the gene transfer efficiency into the chosen target cells could be raised to approximately 1%. However, because adenoviral vectors, in contrast to retroviral vectors, transduce both replicating and non-replicating cells, the estimate of 0.01% gene transfer into cells of the tumor vasculature is more realistic. In any event, administering the adenovector via the circulation is expected to result in at least 99% of the adenoviral vectors interacting and possibly being taken up by cells in normal tissues. This is highly undesirable with respect to toxic side-effects of the procedure. E.g., the introduction and expression of a suicide gene or an inflammation eliciting cytokine gene should obviously not take place in the endothelium of the normal vasculature. Therefore, until the present invention the common belief in the field has been that administering the adenovector to the tumor via the circulation requires some sort of specific targeting of the adenovector to the tumor or its vasculature (e.g., WO 96/25947). Said specific targeting may include specific interaction with and uptake by the intended target cells, as well as specific expression of the introduced genetic information in the intended target cells. Said specific targeting was felt to be necessary to ensure efficient gene transfer and to avoid toxic side-effects in other tissues. Many different molecules that are specifically expressed or upregulated on the cell surface of tumor cells or their vascular endothelial cells have been proposed as targets for specific uptake of gene transfer vectors. Examples of such molecules are carcinoembryonic antigen (CEA; Walther et al., Head-Neck 15:230–235, 1993), surface-bound vascular endothelial growth factor (VEGF; Plate et al., Int. J, Cancer 59(1994):520–529; Brown et al., Hum. Pathol. 26(1995):86–91), the $avb_3$ integrin (Brooks et al., Science 264(1994):569–571), endosialin (Rettig et al., Proc. Natl. Acad.Sci. USA 89(1992):10832–10826) and radiation-induced E-selectin (WO 96/25947). However, said specific interaction with and uptake by the intended target cells is extremely difficult to achieve, for two reasons; i.e. (1) most of the proposed target molecules are also expressed on normal tissue, albeit at lower levels, and (2) it is difficult to construct targeted gene delivery vehicles. Many years of research have been invested by many different investigators in devising targeted gene delivery vehicles for this purpose, without significant success. Perhaps eventually this goal will be reached, but not without a major research effort and significant investment.

As a further alternative way to accomplish functional expression of genetic material in the vasculature of tumors, it has been proposed to transfer said genetic material into cultured endothelial cells ex vivo, followed by administration of said cultured endothelial cells via the circulation (WO 93/13807). This should result in selective incorporation of said cultured endothelial cells at sites of active angiogenesis, including the vasculature of solid tumors. However, such a selective incorporation into the vasculature of solid tumors has not been shown to occur.

Furthermore, the disadvantage of this approach is that it involves the isolation, ex vivo manipulation, and readministration of endothelial cells.

The present invention provides an effective and safe treatment of (solid) tumors in the body of mammals. This is accomplished by administration via the circulation of recombinant adenoviral vectors with wild-type infection spectrum that carry an interleukin-3 gene in a functional format.

Thus the invention provides the use of a recombinant adenoviral vector encoding IL-3 activity for manufacturing a pharmaceutical composition for the systemic treatment of tumors. For the present invention IL-3 activity is defined as the protein itself, derivatives and/or fragments thereof having at least, but preferably most or all of the biological functions of IL-3, although the amounts of activity displayed by these derivatives and/or fragments may vary. It is preferred that the systemic treatment is restricted to certain tissues, organs, or extremities, or certain combinations thereof, because adenovirus is in principle capable of infecting almost any cells in the host, so that the restriction enables to avoid unnecessary infection, as well as higher probability of infection of the proper targets. Thus in a preferred embodiment the invention provides a systemic treatment which includes isolated tissue perfusion. Tissue perfusion is intended to read on isolated tissues as well as organs and/or extremities or any combination thereof. Two approaches of isolated perfusion are provided, one whereby the isolated perfunded tissue includes the tumor and one whereby the isolated perfunded tissue excludes the tumor. In the second case organs or body parts which are liable to be damaged by the treatment or which are likely to influence the uptake of virus by the target cells can be excluded from the system to which the adenoviral vector encoding IL-3 activity is provided. A preferred organ to be excluded according to the invention is the liver.

In the other isolated perfusion route the vector is delivered to the isolated part only. It is preferred to deliver the vector in the form of a virus-like particle.

This means that the vector is packed in an adenovirus shell. The most preferred virus-like particle is the human homolog of recombinant adenovirus IG.Ad.CMV.rIL-3 deposited at the ECACC under accession number V96071634 or a functional derivative thereof.

IL-3 is not only capable of inducing regression of tumors, but it is also capable of retarding or halting the growth of tumors over prolonged periods of time. Many cytostaic agents are also capable of accomplishing regression of tumors, but are not capable of holding the regressed tumor in check over a prolonged period of time. It is therefor advantageous to make combinations of IL-3 activity and other cytostatic activity to have the best of both worlds. Regression of the tumor by administration of one or a number of doses of a cytotoxic agent and obtaining further regression as well as retarding or halting the growth of the regressed tumor by providing IL-3 activity.

Thus the invention further provides a means for treating tumors comprising a pharmaceutical composition comprising Il-3 activity and a pharmaceutical composition comprising cytostatic activity. Preferably, the IL-3 activity is provided by a recombinant adenoviral vector, (preferably in a virus-like particle) encoding said activity to be given systemically, either in an isolated perfusion format or not. Preferably the pharmaceutical composition comprising cytostatic activity is in a single dosage unit for injection into a solid tumor, to be given once or several times until the required dosage is reached.

Typically the virus-like particle is present in an amount of from about $10^6$ to $5.10^9$ iu in a perfusion fluid.

It is of course also possible that both activities are present in one composition.

Preferably the cytostatic or cytotoxic activity is TNF-activity, Melphalan, or adriamycin. The invention further provides a pharmaceutical composition for systemic treatment of tumors comprising IL-3 activity provided by a recombinant adenoviral vector encoding such activity, whereby said pharmaceutical composition is a perfusion fluid. Preferably the recombinant adenoviral vector is provided in the form of virus-like particles. Preferably said virus-like particles are present in an amount of about $10^6$ to $510^9$ iu.

The most preferred virus is the human homolog of recombinant adenovirus IG.Ad.CMV.rIL-3 deposited at the ECACC under accession number V96071634 or a functional derivative thereof.

The invention further provides a kit of parts for the treatment of tumors comprising a pharmaceutical composition comprising IL-3 activity, means for isolating certain tissues, and means for perfunding said isolated tissues. Hereby the essential elements for performing a method of treatment according to the invention are given. The means for perfunding are preferably heart-lung machines or other equipment capable of perfunding and preferably oxygenating. Means for excluding certain organs, limbs and/or tissues are known in the art and references thereto can be found herein. If it is possible to exclude then it is of course also possible to limit perfusion to said organs, tissues or limbs which can be excluded. Of course the IL-3 activity in the kit of parts is again preferably provided by a recombinant adenoviral vector encoding said activity, preferably in the form of a virus-like particle, preferably present in an amount of about $10^6$ to $5.10^9$ iu. Preferably the kit of parts further comprises a pharmaceutical composition comprising cytostatic activity for the reasons already disclosed herein.

DETAILED DESCRIPTION OF THE INVENTION

Despite the high potential of cancer gene therapy, the results of experimental treatment of solid tumors have until now been very disappointing. Direct injection of gene delivery vectors, mostly adenoviral vectors, carrying therapeutic genetic information into solid tumors has resulted in efficient gene transfer into tumor cells and has shown some, although still incomplete, tumor regression (e.g., see patent applications WO 95/05835 and EP 0 707071). The major limitation of this approach, however, has been that every solid tumor has to be individually injected. This makes clinical application of such a treatment far from realistic for most cancers, in particular for advanced cancers with metastases. The alternative approach, i.e. therapeutic gene delivery via the circulation after systemic intravascular administration of said gene delivery vector, has been associated with extremely low gene transfer efficiency into the tumor. The common belief in the field has been, therefore, that the gene transfer efficiency should be increased to obtain a significant therapeutic effect. It is also generally accepted that this should not be done by administering more gene delivery vectors, but by promoting the specific uptake of said gene delivery vector into the tumor cells or into the endothelial cells aligning the tumor vasculature. The reason for this is that high concentrations of untargeted gene delivery vectors cause (1) a stronger immune response, and (2) more toxicity due to delivery of the anti-tumor gene to other tissues. Furthermore, it is difficult and expensive to produce extremely high concentrations of gene delivery vectors.

The present inventors have made the surprising observation that adenoviral vector mediated delivery of an interleukin-3 gene through administration via the circulation into the vasculature of solid tumors results in a very effective cancer treatment. Said circulation is meant to include both the blood circulation and the lymphatic circulation. Said adenoviral vector is not treated in any way to promote its specific uptake by the solid tumor cells or the endothelial cells aligning the tumor vasculature. The therapeutic effect of said delivery is much more dramatic than could be expected from the low transduction efficiency (less than 1% transduced cells) that is obtained with said administration via the circulation. Established solid tumors growing in relevant animal models regressed completely. Said therapeutic effect is shown to be dependent on both said administration via the circulation and the biological activity of the interleukin-3 encoded by the introduced gene.

The present invention among other things provides a recombinant adenoviral vector that carries a nucleic acid molecule that encodes interleukin-3 or a functional derivative or a fragment thereof. Said nucleic acid molecule is provided with a format that allows functional expression of said interleukin-3 in solid tumor cells and/or in endothelial cells of the vasculature of a solid tumor in the body of a mammal after administration of said recombinant adenoviral vector to the circulation of said mammal. The term "functional expression" is understood to mean production of said interleukin-3 with biological activity that leads to killing of said solid tumor cells. Said format is conferred upon said nucleic acid molecule by including upstream of said nucleic acid molecule an activator (promoter and/or enhancer) nucleic acid molecule that preferably interacts with one or more trans-activating transcription factors that are present in tumor cells or in cells of the vasculature of a tumor and downstream of said nucleic acid molecule a eukaryotic polyadenylation signal. Said activator molecule may be derived from the adenovirus used to construct said adenoviral vector or from a different adenovirus. Alternatively, said activator molecule is of exogenous origin. Useful activator molecules in this aspect of the invention are derived from, e.g. the Cytomegalovirus Immediate Early promoter/enhancer, the Rous Sarcoma Virus LTR promoter/enhancer, but may also be derived from other activator molecules known in the art. In this aspect of the invention it is preferred that said nucleic acid molecule encoding interleukin-3 is a functional derivative from or includes at least a functional fragment of a nucleic acid molecule isolated from the same species as said mammal. Because in most applications of the invention said mammal is a human, it is in most applications of the invention preferred that said nucleic acid molecule is a functional derivative from or includes at least a functional fragment of a nucleic acid molecule isolated from a human. The terms "functional derivative" and "functional fragment" are used here to indicate that said nucleic acid molecule encodes a peptide molecule with the same biological activity in kind, but not necessarily in amount, as said interleukin-3.

Many different examples of nucleic acid molecules encoding mutants of human interleukin-3 with functional interleukin-3 activity are given in European patent EP 0 413 383. It is furthermore preferred that the biological activity of said interleukin-3 includes the elicitation of an intense local inflammation associated with an inflammatory type cell infiltration. The recombinant adenoviral vectors according to the invention may be derived from any wild-type adenovirus serotype that allows the functional expression of said interleukin-3 in solid tumor cells and/or in endothelial cells of the vasculature of a solid tumor in the body of a mammal after administration of said recombinant adenoviral vector to the circulation of said mammal. In the examples given infra to illustrate the present invention said recombinant adenoviral vectors are derived from human adenovirus type 5. It is to be understood, however, that those skilled in the art will be able to apply other recombinant adenoviral vectors without departing from the invention. Methods for the construction of recombinant adenoviral vectors according to the invention and for their propagation on useful packaging cells have been described in patent applications EP 0 707 071 and WO 97/00326, incorporated herein by reference. Other examples of vectors and packaging systems useful in the invention include, but are not limited to, those given in patent applications WO 93/19191, WO 94/28152, WO 96/10642, and WO 97/04119.

The present invention furthermore provides a pharmaceutical composition that comprises the recombinant adenoviral vector defined supra in combination with a diluent that is not toxic to the recipient mammal at the dosage used and that retains sufficient stability of the infectivity of said recombinant adenoviral vector for a time long enough to allow uptake of said recombinant adenoviral vector into the solid tumor cells and/or endothelial cells of the vasculature of a solid tumor after administration of said composition to the circulation of the recipient mammal.

A typical non-limiting example of a diluent according to this aspect of the invention is an isotonic saline solution that is sterile and that is buffered at a physiological pH. Preferably, said diluent furthermore contains serum-substituting ingredients. In the examples given infra to illustrate the present invention Haemaccel (Behring Pharma) is used as a suitable diluent. It is to be understood, however, that those skilled in the art will be able to apply other diluents without departing from the invention. For some applications of the invention it is furthermore preferred that said pharmaceutical composition is oxygenated prior to administration. Optionally, said recombinant adenoviral vector (or virus) is prepared in lyophilized form. In the latter case, said recombinant adenoviral vector is suspended in solution to obtain said pharmaceutical composition before administering said pharmaceutical composition to the circulation of the recipient mammal. Typically, a pharmaceutical composition comprising one dose contains at least about $10^6$, preferably about $10^8$ infectious units (iu) of the adenoviral vector of the invention, but in certain conditions it is preferred that it contains at least about $10^9$, more preferred $10^{10}$, or even more preferred $10^{11}$ iu. The amount of virus to be provided depends on many parameters. As disclosed herein only a very limited portion of the administered virus actually infects the target cells. This may be one reason to increase the amount of virus to be administered. Also the size of the tumor and/or the degree of its vascularization will influence the amount of virus required to get an effect. Another important aspect is of course the amount of IL-3 activity expressed by a cell infected with one or more viruses. This of course depends on the cell, but also on the promoter that drives the expression and its interaction with cell components of the expression machinery, etc.

Based on the rat studies, where a CMV promoter is driving the rat IL-3 gene, anti-tumor activity was measured after perfusion with $10^9$ i.u. of IG.Ad.CMV.rIL-3. Perfusion time was 15 minutes. The size of this tumor was approximately 1 cm$^3$. Dose finding studies are performed, where the range of administered [perfused] will increase from $10^6$ up to $10^{10}$ iu. Anti-tumor activity is measured according to the methods described. The lowest dose resulting in a maximal anti-tumor effect will be used to calculate the dose to be delivered to human tumors, assuming that the same promoter are used in the adenoviral vector harboring the human IL-3 gene or a derivative thereof. It is assumed that the infection of human cells by recombinant adenoviral vectors is 10× more efficient than rat cells. Furthermore, we assume the vascular bed or the tumor to be proportional to the tumor volume. Therefore, the optimal dose assessed in the rat model is extrapolated to the human situation by the following calculation:

$$\text{dose delivered to humans} = \frac{[\text{effective dose in rat}] \times [\text{tumor volume (human)}]}{[10 \times \text{tumor volume (rat)}]}$$

In another aspect, the invention provides a method to deliver said nucleic acid molecule that encodes interleukin-3 to solid tumor cells and/or endothelial cells of the vasculature of a solid tumor in the body of a mammal, whereby the adenoviral vector or pharmaceutical composition defined supra is administered to a site in the circulation of said mammal. Said circulation is meant to include both the blood circulation and the lymphatic circulation. Thus, the administration is performed to any site in the body of the recipient mammal where the blood or lymph fluids of said mammal pass. Preferred sites of administration are intravenous or intra-arterial, where it is further preferred that said administration is into an artery located upstream of the tumor vasculature. There are several means to perform said administration to the circulation. One of said means is by injection using, e.g., a syringe, a catheter or another infusion system known in the art. Preferably, said injection is performed at a controlled infusion rate. A much preferred means to perform said administration to the circulation is by perfusion. Perfusion is a technique whereby said administered pharmaceutical composition is caused to pass through said circulation or through a part of said circulation. When the administration is performed by perfusion it is furthermore preferred that said perfusion is done multiple times by creating a closed circuit and repassaging said pharmaceutical composition through said circulation or said part of circulation. Typically, said causing to pass is done by using a pump device and perfusion is performed at a rate depending on the species of the mammal to which said pharmaceutical composition is being administered. For humans, said rate is often in the range of approximately 40–80 ml/min and said perfusion is continued for a period of 60–90 minutes, but depending on patient, type of tumor, location thereof, these parameters may vary. For short treatment times (approximately 5–30 minutes) with the adenoviral construct an anoxic perfusion can be performed by those skilled in the art by using balloon catheters to make a closed circuit. No heart-lung machine is necessary.

In this aspect of the invention, said part of the circulation comprises the vasculature of the tumor or tumors to which gene delivery is performed. For optimal delivery of said nucleic acid molecule that encodes interleukin-3 to solid tumor cells and/or endothelial cells of the vasculature of a solid tumor it is preferred that the adenoviral vector or composition of the invention does not pass through the liver or a part of the liver of the recipient mammal. Thus, said part of the circulation does preferably not include the circulation of the liver or of a part of the liver, except when the tumor is located in or very close to the liver. For optimal delivery of said nucleic acid molecule that encodes interleukin-3 to solid tumor cells and/or endothelial cells of the vasculature of a solid tumor it is furthermore preferred that the blood of the mammal is first washed away from said closed circuit (e.g., by precirculation with the diluent of the pharmaceutical composition only) before said pharmaceutical composition is administered. Optionally, the blood that is washed away is collected and readministered at the end of the procedure. Surgical techniques for perfusion of parts of the circulation according to the present invention are under development and are already available for various specific parts of the circulation, such as, e.g., the liver (Fraker, D L et al., Circulatory shock, 44, p.45–50, 1994), the lung (Progrebniak H W et al., Ann. Thorac. Surg.,57, p.1477–83, 1994), and the kidney (Veen van de AH et al., Eur. J. Surg. Oncol. 20, p.404–405, 1994). A typical nonlimiting example of a routine perfusion technique useful in the invention is isolated limb perfusion (ILP), where a closed circuit is created between the femoral artery and the femoral vein. Alternatively, essentially the same perfusion techniques can be employed in the invention to exclude the delivery of said nucleic acid molecule to a part or parts of the circulation. In this aspect of the invention, the part or parts of the circulation to which said delivery is unwanted are perfused with a diluent according to the invention while said pharmaceutical composition is administered to the circulation systemically (hence, outside the perfusion circulation). An important example of this embodiment of the invention is exclusion of the liver circulation from delivery of said nucleic acid molecule.

The invention furthermore provides genetically modified solid tumor cells and cells of the vasculature of a solid tumor expressing said interleukin-3 in the body of a mammal. These cells expressing said interleukin-3 are obtained by administering the composition containing the adenoviral vector according to the invention using the method according to the invention via the circulation of said mammal.

The expression of said interleukin-3 in said solid tumor cells or cells of the vasculature of a solid tumor results in an effective killing of said cells. Thus, the present invention also provides a gene therapy treatment for solid tumors. All tumors that are in close contact with the circulation can be treated according to the invention. Although leukemias and lymphomas are not excluded, vascularized solid tumors are especially suited for treatment according to the invention. Examples of types of said solid tumors include, but are not limited to, carcinomas (e.g., of the lung, bladder, kidney, breast, stomach, pancreas, urogenital tract, and intestine), sarcomas (e.g., soft tissue sarcomas, osteogenic sarcomas, or Kaposi's sarcoma), gliomas and melanomas. Also benign types of tumors, such as, e.g., angiomas and fibrocytomas can be treated according to the invention. It is to be understood, however, that the scope of the present invention is not to be limited to the treatment of any particular type of tumor.

It is furthermore to be understood that the cancer treatment according to the invention may be combined with other methods of cancer treatment known in the art. Such treatment combinations are also part of the present invention.

The invention is illustrated by means of the following examples. It is to be understood that said examples are not meant to limit the scope of the invention in any way.

Example 1 teaches the production of adenoviral vectors and pharmaceutical compositions according to the invention.

Example 2 teaches the cloning and production of an adenoviral vector with the human IL-3 gene and the pharmaceutical composition according to the invention.

Example 3 and 4 show the gene transfer efficiency that is obtained when adenoviral vectors are administered to a solid tumor via the circulation or by direct intra-tumor injection, as well as the unwanted gene transfer into non-tumor cells in both cases, and the type of cells in the tumor that are transduced using these administration methods. It is shown that the direct injection results in approximately 87-times more expression of the introduced gene in the tumor than administration via the circulation. The direct injection efficiently transduces many tumor cells along the needle tract, whereas administration via the circulation mainly transduces endothelial cells of the tumor vasculature, a few solid tumor cells adjacent to the vascular endothelial cells and some cells in or near the capsule of the tumor. Gene transfer into tissues other than the tumor hardly occurs using either method.

Examples 5, 6, 7 and 8 clearly demonstrate the effective anti-tumor effect that is accomplished by administering an adenoviral vector carrying the interleukin-3 gene into two types of solid tumors via the circulation. Complete regression of said tumors occur. Experiments show that this effective anti-tumor effect is not obtained by direct intra-tumor injection or by using an adenoviral vector that expresses the IL-3 gene at low levels. Control isolated limb perfusion experiments show that this effective anti-tumor effect is not obtained by a isolated limb perfusion without addition of said adenoviral vector with the interleukin-3 gene or by treatment with an adenoviral vector without effector gene. After the latter treatment some delay in tumor growth is observed when ROS-1 osteosarcomas were used, but the tumors do not regress. The latter growth delay is not observed when BN175 tumors were treated. Example 5 shows that the anti-tumor effect is specific for the activity of the interleukin-3 gene. Anti-cancer treatment by administering adenoviral vectors expressing the HSV-tk gene via the circulation followed by ganciclovir injections show only incomplete effects.

Example 9, 10 and 12 demonstrate that in the rats with the two tumor models studied the optimal dose for administering of the adenoviral vector carrying the interleukin-3 gene via the circulation is $1.0^9$ iu (infectious units). And that a 15 minutes perfusion results in good antitumor effects.

Example 11 clearly demonstrates that the administration via the circulation of $1.10^9$ iu of the adenoviral vector carrying the interleukin-3 gene is at least as efficient as the established combination therapy with TNF( and Melphalan).

EXAMPLES

Example 1

Generation of recombinant adenoviral vectors and production of pharmaceutical compositions containing said recombinant adenoviral vectors for administration via the circulation of a mammal.

The cloning, sequence analysis and generation of E1 deleted adenovirus vectors has been described in detail in patent application EP 95 20 2213 incorporated herein by reference. The adenovirus vector is deleted for the E1, but the E3 region was retained in this vector. The gene is driven by the Cytomegalovirus promoter (CMV) or the adenovirus-2 derived Major late promotor (MLP). The names of the viruses are IG.Ad.CMV.rIL-3 (this vector contains the rat IL-3 cDNA), IG.Ad.MLP.Luc (this vector contains the luciferase marker gene), IG.Ad.CMV.LacZ (this vector contains the LacZ marker gene) and Ad.CMV.TK (this vector contains the TK (thymidine kinase) gene). Recombinant adenovirus IG.Ad.CMV.rIL-3 has been deposited at the ECACC under accession number V96071634. The generation and propagation of these vectors on E1 complementing cell lines has been described in patent application EP 95 20 2213 and in references Esandi et al. (1997), Vincent et al. (1996a, 1996b). Propagation of the vectors on E1 complementing PER.C6 is described in patent application WO 97100326. The PER.C6 cell line has been deposited at the ECACC under deposition number 96022940. After propagation, the recombinant viruses were purified by CsCl density centrifugation and dialyzed according to standard procedures. Titration of the viruses was performed by end-point dilution on 911 cells. The vectors are stored in phosphate buffered saline (PBS) supplemented with 10 % (v/v) glycerol or 5% (w/v/) sucrose and stored at −80° C.

Example 2

Generation of a recombinant adenoviral vector with the human IL-3 gene (pAd5.CLIP.hIL-3) and production of pharmaceutical compositions containing said recombinant adenoviral vector (IG.Ad5.CLIP.hIL-3) for administration via the circulation.

2.1.1. Generation of the Adenoviral Vector pAd5.CLIP

The pAd5.CLIP adenoviral vector contains a deleted E1 gene, but the E3 region was retained in this vector. Said adenoviral vector consists of a Cytomegalovirus promoter (CMV1, polylinker, intron and polyA sequence. For those skilled in the art it is possible to insert in the polylinker site of the pAd5.CLIP vector any piece of DNA of interest. In this case the human interleukin-3 coding sequence was inserted (as described in example 2.2). The cloning strategy of the pAd5.CLIP adenoviral vector is shown in FIG. 1 and described below. PcDNA1 (Life Technologies) was digested with the restriction enzymes HhaI and AvrII. The sticky ends of the 1567 bp fragment were filled in with the enzyme T4-polymerase. The plasmid pAd/L420-HSA (the generation of this adapter plasmid is described in the next subparagraph of this example ($2.1.2)) was digested with the restriction enzymes AvrII and BglII followed by treatment with Klenow polymerase (Life Technologies) resulting in a 5.5 kb DNA fragment. The purified 5.5 kb pAd/L420-HSA fragment was dephosphorylated with Tsap (Thermo Sensitive Alkaline Phosphatase, Life Technologies) and ligated with the purified 1.5 kb pcDNA1/Amp/HhaI/AvrII fragment. The ligation product was added to transformation competent DH5 (E.coli cells and plated on ampicilin containing plates. The resulting pAd5.CLIP plasmid DNA was isolated and checked by restriction digestion analysis.

2.1.2. Construction of the Adapter Plasmid pAd/L420-HSA

The absence of sequence overlap between the recombinant adenovirus and E1 sequences in the packaging cell line is essential for safe, RCA-free generation and propagation of new recombinant viruses. The adapter plasmid pMLPI.TK was designed for use according to the invention in combination with the improved packaging cell lines of the invention. The plasmid pAd/L420-HSA is a derived out of the adapter plasmid pMLPI.TK. The construction strategy is described below (paragraph 2.1.2.1 and 2.1.2.2).

2.1.2.1. Construction of pMLPI.TK

The recombinant adenovirus vectors used (pE1A.E2B, pMLP.TK, see patent application EP 95/202213) are E1B deleted for E1 sequences from nt. 459 to 3328. As construct pE1A.E1B contains Ad5 sequences nt. 459 to 3510 there is a sequence overlap of 183 nt between E1B sequences in the packaging construct pIG.E1A.E1B. and recombinant adenovirusses, such as for example IG.Ad.MLP.TK. The overlapping sequence were deleted from the new adenoviral vectors. In addition, non-coding sequences derived from LacZ, that are present in the original constructs, were deleted as well. This was achieved (see FIG. 15) by PCR amplification of the SV40 poly(A) sequences from pMLP.TK using primers SV40-1 (5'-GGGGGATCCGAACTTGTTTATTGCAGC-3'(SEQ ID NO.1): introduces a BamHI site) and SV40-2 (5'-GGGAGA TCTAGACATGATAAGATAC-3'(SEQ ID NO.2): introduces a BglII site). In addition, Ad5 sequences present in this construct were amplified from nt. 2496 using primer Ad5-1 (GGGAGATCTGTACTGAAATGTGTGGGC-3'(SEQ ID NO.2): introduces a BglII site) to nt. 2779 using primer Ad5-2 (5'-GGAGGCTGCAGTCTCCAACGGCGT-3'(SEQ ID NO.4)). Both PCR fragments were digested with BglII and were ligated. The ligation product was PCR amplified using primers SV40-1 and Ad5-2 (sequence described above). The PCR product obtained was cut with BamHI and AflII and was ligated into pMLP.TK predigested with the same enzymes. The resulting construct, named PMLPI.TK, contains a deletion in adenovirus E1 sequences from nt. 459–3510.

2.1.2.2. Construction of the pAd/L420-HSA Adapter Plasmid

The pMLPI.TK plasmid was used as the staring material to make a new vector in which nucleic acid molecules comprising specific promoter and gene sequences can be easily exchanged. First, a PCR fragment was generated from pZip(Mo+PyF101 (N-) template DNA (described in PCT/NL96/00195) with the following primers: LTR-1:5'-CTGTA CGTACCAGTGCACTGGCCTAGGCATGGAAAAATA CATAACTG-3'(SEQ ID NO.5 ) and LTR-2: 5'-GCGGA TCCTTCGAACCATGGTAAGCTTGGTACCGCTAGCG TTAACCGGGCGACTCAGTCAATCG-3'(SEQ ID NO.6). Pwo DNA polymerase (Boeringer Mannheim) was used according to the manufacturer's protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once 10 minutes at 72° C. The PCR product was then digested with BamHI and ligated into a pMLP10 (Levrero et al. (1991). Gene 101: 195–202) vector digested with PvuII and BamHI, thereby generating vector PLTR10. This vector contains adenoviral sequences from bp 1 up to bp 454 followed by a promoter which includes part of the Mo-MuLVLTR in which the wild-type enhancer sequences are replaced by the enhancer from a mutant polyoma virus (PyFlol). The promoter fragment was designated L420. Next, the coding region of the murine HSA-gene was inserted. pLTR10 was digested with BstBI followed by Klenow treatment and digestion with NcoI. The HSA-gene was obtained by PCR amplification of pUC18-HSA (Kay et al. (1990). J.Immunol. 145:1952–1959.) using the following primers: HSA1: 5'-GCGCCACCATGGGCAGAGCGATG GTGGC-3'(SEQ ID NO.7) and HSA2: 5'-GTTAGATC TAAGCTTGTCGACATCGATCTACTAACAGTAGAGA TGTAGAA-3'(SEQ ID NO.8). The 269 bp amplified fragment was subcloned in a shuttle vector using the NcoI and BglII sites. Sequencing confirmed incorporation of the correct coding sequence of the HSA-gene, but with an extra TAG insertion directly following the TAG stop codon. The coding region of the HSA-gene, including the TAG duplication was then excised as a NcoI(sticky)-SalI(blunt) fragment and cloned into the 3,5 kb NcoI (sticky)/BstI (blunt) fragment from pLTR10, resulting in pLTR-HSA10. Finally, PLTR-HSA10 was digested with EcoRI and BamHI after which the fragment containing the left ITR, packaging signal, L420 promoter and HSA-gene was inserted into vector PMLPI.TK, digested with the same enzymes, thereby replacing the promoter and the gene sequences. This resulted in the new adapter plasmid pAd/L420-HSA. (FIG. 16) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from the HSA-coding region to replace genes in this construct.

2.2. Generation of pAd5.CLIP.hIL-3

PcDNA3.hIL-3 (patent number W088/04691, Gist Brocades (GB)) was digested with the restriction enzymes HindIII and BamHI to obtain a 1 kb fragment that contains the functional hIL-3 sequence (hIL-3/BamHI/HindIII(GB)). The plasmid pAd5.CLIP was digested with BamHI and HindIII (in the multiple cloning site) and purified. Next the pAd5.CLIP/BamHI/HindIII DNA was dephosphorylated by Tsap. The pcDNA3.hIL-3/BamHI/HindIII and pAd5.CLIP/BamHI/HindIII DNA fragments were ligated and the ligation product was added to transformation competent DH5( E.coli cells. The pAd5.CLIP.hIL-3(GB) plasmid DNA was isolated and checked by a digestion with EcoRI. Because of possible unknown sequences at the HindIII site of the hIL-3 gene (pcDNA3.hIL-3 plasmid generated previously by Gist Brocades) and the presence of a polyA tail on the BamHI site, the hIL-3 cDNA coding sequence is amplified out of the pAd5.CLIP.huIL-3(GB) by means of PCR. The primers used: huIL3-forward: CCCCAAGCTTGCCACCATGAGC-CGCCTGCCCGTC (SEQ ID NO.9) and huIL3-reverse: GCGGGATCCTCAAAAGATCGCGAGGC (SEQ ID NO.10) (Life Technologies). The PCR product (484 bp) was digested with the restriction enzymes BamHI and HindIII and the huIL-3/BamHI/HindIII(PCR) fragment (475 bp) was cloned in pAd5.CLIP.HindIII/BamHI. Plasmid DNA was obtained via transformation of competent DH5( E.coli cells. The 7131 bp construct is termed: pAd5.CLIP.hIL-3. The DNA was checked by restriction enzym and sequence analysis. The expression and biological activity of the hIL-3 transgene was shown by transfection of the human PERC6 cell line (patent number WO 97/1000326, ECACC no. 96022940) with the pAd5.CLIP.hIL-3 plasmid followed by a hIL-3 protein ELISA (Quantikine kit, R&D) and hIL-3 bioactivity assay using TF-1 cells (human IL-3 protein dependent for their growth) of the secreted hIL-3 protein in the PERC6 culture medium. The data of these two experiments (huIL-3 ELISA, TF-1 bioactivity assay) are shown in FIG. 17.

2.3. Generation of Recombinant Adenovirus (IG.pAd5.CLIP.hIL-3)

A general protocol as outlined below and meant as a non-limiting example of the present invention has been performed to produce the IG.pAd5.CLIP.hIL-3 recombinant adenovirus. Adenoviral packaging cells (PER.C6) were seeded in 25 cm² flasks and the next day when they were at approx. 80% confluency the cells were transfected with a mixture of DNA and lipofectamine agent (Life Technologies) as described by the manufacturer. Routinely, 40 μl lipofectamine, 4 μg adapter plasmid and 4 μg of the complementing adenovirus genome fragment AFLII-rITR were used. Two days later, cells were passaged to 80 cm² flasks and further cultured. Approximately five days later a cytopathic effect (CPE) was observed, indicating that functional adenovirus has been formed. Cells and medium were harvested upon full CPE and recombinant IG.pAd5.CLIP.hIL-3 adenovirus was released by freeze-thawing. An extra amplification step in a 80 cm² flask was performed to increase the yield. After amplification, viruses were harvested and plaque purified on PER.C6 cells. Individual plaques were tested for production of viruses with the active IL-3 transgene by the hIL-3 ELISA and TF-1 bioactivity assay as described above. Functional IG.pAd5.CLIP.hIL-3 adenovirus was formed with an active IL-3 transgene. Propagation of the vector on E1 complementing PER.C6 cells is described in patent application WO 97/100326. The PER.C6 cell line has been deposited at the ECACC under deposition number 96022940. After propagation, the recombinant IG.pAd5.CLIP.hIL-3 adenovirus was purified by CsCl density centrifugation and dialyzed according to standard procedures. Titration of the viruses was performed by end-point dilution on 911 cells. The vector is stored in phosphate buffered saline (PBS) supplemented with 10% (v/v) glycerol or 5% (w/v) sucrose and stored at −80° C.

Example 3

Comparison of gene transfer efficiencies that are achieved using recombinant adenoviral vectors that are administered either by perfusion of the circulation of a tumor or by direct intra-tumor injection.

3.1. Tumor Models

The BN175 sarcoma (Marquet et al (1983), Kort et al. (1984)) originated as a spontaneous tumor in the pancreatic, retroperitoneal region of a BN rat. The BN175 was implanted subcutaneously in the flank of donor BN rats and passaged serially. BN175 is a non-immunogenic (Manusama (1996)), rapidly growing and metastazing tumor with a tumor doubling time of 2 days. The rapidly growing ROS-1 osteosarcoma originated spontaneously in the tibia of a Wag/Rij rat (Barendsen et al. (1987)). The ROS-1 was implanted subcutaneously in the flank of donor Wag/Rij rats and passaged serially. The ROS-1 has a tumor doubling time of 5 days.

Fragments of the BN175 or ROS-1 (osteo)sarcoma were subcutaneously implanted into the right hindlimb of the experimental animals just above the ankle. The tumor size was measured regularly by caliper measurement in two dimensions. When the tumor reached a volume of 180–524 mm³ (diameter between 7 and 10 mm) an isolated limb perfusion (ILP) with the recombinant adenoviral vector was performed. As a control, tumor bearing rats underwent ILP without the addition of said recombinant adenoviral vectors (termed sham ILP). An other group of tumor bearing rats underwent a direct intra-tumor injection with said recombinant adenoviral vector. The tumor volume was between 180–524 mm³). After ILP or direct intra-tumor injection the tumor size was measured every (mon-fri)day.

3.2. Surgical and Perfusion Techniques

Surgical procedures were performed under Hypnorm anaesthesia. (Janssen Pharmaceutica, Tilburg, The Netherlands) For isolated limb perfusion (ILP) a modification of the perfusion technnique originally described by Brenckhuijsen et al. (1982) was used (Manusama et al. (1996)). After an incision parallel to the inguinal ligament the femoral and vein were approached and cannulated with silastic tubing (0.30 mm ID, 0.64 mm OD; 0.64 mm, 1.19 OD, respectively, Degania Silicone, Degania Bet, Israel). Collaterals were temporarily occluded by the application of a tourniquet around the groin, which was fixed to the inguinal ligament. An oxygenation reservoir and a roller pump (Masterflex) were included in the vascularly isolated circuit, which was, initially, perfused with haemaccel (Behring Pharma, Amsterdam, The Netherlands) for 3 minutes at a flow speed of 2 ml/min to wash out the blood. After the first wash out step, recirculation was performed with recombinant adenoviruses (50 µl-1 ml, containing approximately $10^9$ infectious units (i.u.)) dissolved in 2.5–3.5 ml Haemaccel at the same flow rate for a time period ranging from 5 to 30 minutes. Followed by a second perfusion step of 5 minutes to wash out the non-bound virus with Haemaccel. During the perfusion and recirculation steps the rat hind leg was kept at a constant temperature of 37–38°, a warm water mattres was applied around the leg. After the second wash-out step, the vascularly isolated circuit was discontinued and, after cannule removal, the femoral vessels were ligated. Previous experiments have shown that the collateral circulation via the iternal iliac artery to the leg is so extensive that ligation of the femoral vessels can be performed without detrimental effects.

3.3.Results

The ILP or a direct intra-tumour injection was performed as described above with 50 ul (containing approx. $5.10^8$ i.u.) of IG.Ad.MLP.Luc. Two days after the ILP or direct intratumoral injection the rats were sacrificed and the tumor was removed. The luciferase activity was determined as described before (Fortunati et al., 1996). The luciferase activity was expressed in amount of luciferase units per total volume of tumor lysate.

TABLE I

Effectivity of the transfer of adenoviral vector containing the Luciferase marker gene to a BN175 tumor via ILP or direct intra-tumor injection.

| perfusion time: (min) | luciferase activity: | No. rats |
|---|---|---|
| 5 | 2039 ± 1197 | 6 |
| 15 | 4835 ± 2448 | 6 |
| 30 | 5647 ± 3308 | 6 |
| intratumoral injection | 422296 ± 271179 | 6 |

The luciferase activity is given as the mean value of 6 experiments ±S.D.

Conclusion

Direct intra-tumor injection results in a 87-fold higher expression of the luciferase activity in the tumour than ILP for 15 min.

ILP for 15 minutes results in an acceptable level of luciferase activity in the tumor compared to 30 minutes of ILP. Therefore, 15 min of ILP is used throughout the experiments.

TABLE II

Transfer of adenoviral vector containing the Luciferase marker gene to other organs after ILP or direct intra-tumor injection.

| perfusion time: | Luciferase activity: | |
|---|---|---|
| No. Of rats: (min) | Liver: | Skeletal muscle of the isolated limb: |
| 5 | 65 | 138 | 6 |
| 15 | 51 | 178 | 6 |
| 30 | 69 | 211 | 6 |
| intra-tumor injection | 38 | 196 | 6 |

The luciferase activity is given as the mean value of 6 experiments.

Conclusion

No high uptake of IG.Ad.MLP.Luc by the liver or skeletal muscle of the isolated limb after ILP or intra-tumor injection.

Example 4.

Histocytological examination of the transduced cells in a tumor after administration of a recombinant adenoviral vector by either perfusion of the circulation of said tumour or direct injection into said tumor.

The ILP or direct intra-tumor injection of BN175 tumor bearing BN rats with $5.10^8$ or $1.10^{10}$ iu IG.Ad.CMV.LacZ was performed as described above. Two days after treatment the animals were sacrificed and tumors were removed. In these tissues the lacZ positive cells were localized by staining with X-gal as described in detail before (Bout et al., 1994).

Briefly, tumors were cut into slices of approximately 5 mm thickness, fixed for 2–3 hours in PBS containing 2% paraformaldehyde and 0.25% glutaraldehyde. After staining with X-gal, the tissue was post-fixed in 4% phosphate buffered formalin and embedded in paraffin. 5 µm sections were prepared according to routine histochemical methods. The sections were examined microscopically for the presence of blue (=LacZ positive) cells.

Results

Direct injection of the tumors with IG.Ad.CMV.L4cZ resulted in staining along the track of the needle.

Staining of the tissues after ILP showed no blue color in the tumor. The color was restricted to the areas directly adjacent to the blood vessels of the tumor including the endothelial cells and in or near the capsule of the tumor.

The amount of blue stained cells was much larger in the direct intratumoral injected tumors than in the ILP treated tumors.

Example 5

Effect of direct intra-tumor injection or administration via the circulation (isolated limb perfusion) of an adenoviral vector carrying the thymine kinase gene.

Figure 2:
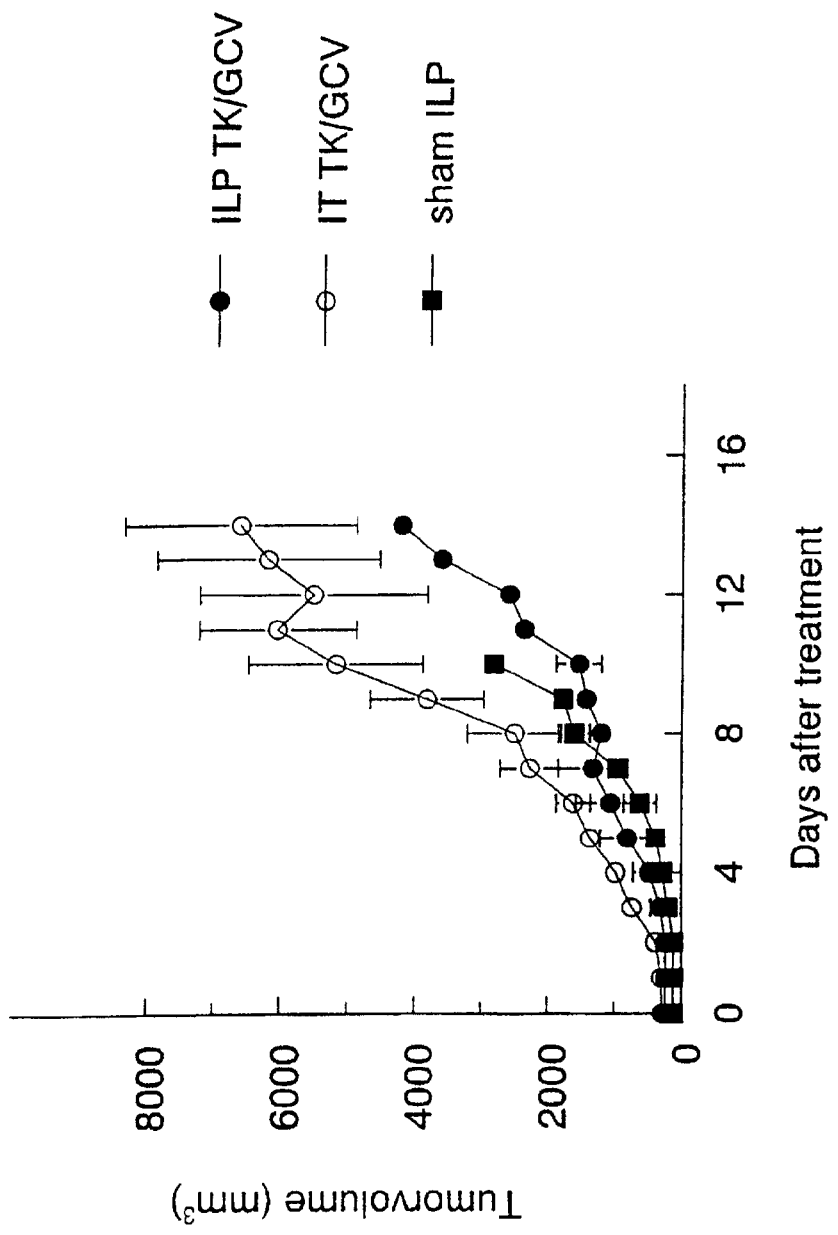

Rats bearing a BN175 tumor in their hindlimb (as described in example 3.1) underwent ILP with 100 ul of IG.Ad.CMV.TK (approx. $1.10^9$ iu) followed by intraperitoneal injection twice a day of ganciclovir (GCV). The tumor sizes were followed in time. The results are depicted in FIG. 2. Another group of BN rats were injected intra-tumorally in the BN175 tumor with 100 ul of IG.Ad.CMV.TK followed by intraperitoneal injection twice a day of ganciclovir (GCV). The tumor sizes were followed in time. The results are depicted in FIG. 2.

Other rats underwent ILP without the addition of virus (control perfusion termed 'sham ILP'). The tumor sizes were followed in time. The results are depicted in FIG. 2.

Results and Conclusions

Isolated limb perfusion (ILP) with TK/GCV (suicide gene therapy) is not effective neither is a control ILP (sham ILP) without the addition of virus.

Example 6

Effect of direct intra-tumoral injection or administration via the circulation (isolated limb perfusion) of BN175 sarcomas with an adenoviral vector carrying the interleukin-3 gene.

Figure 3:
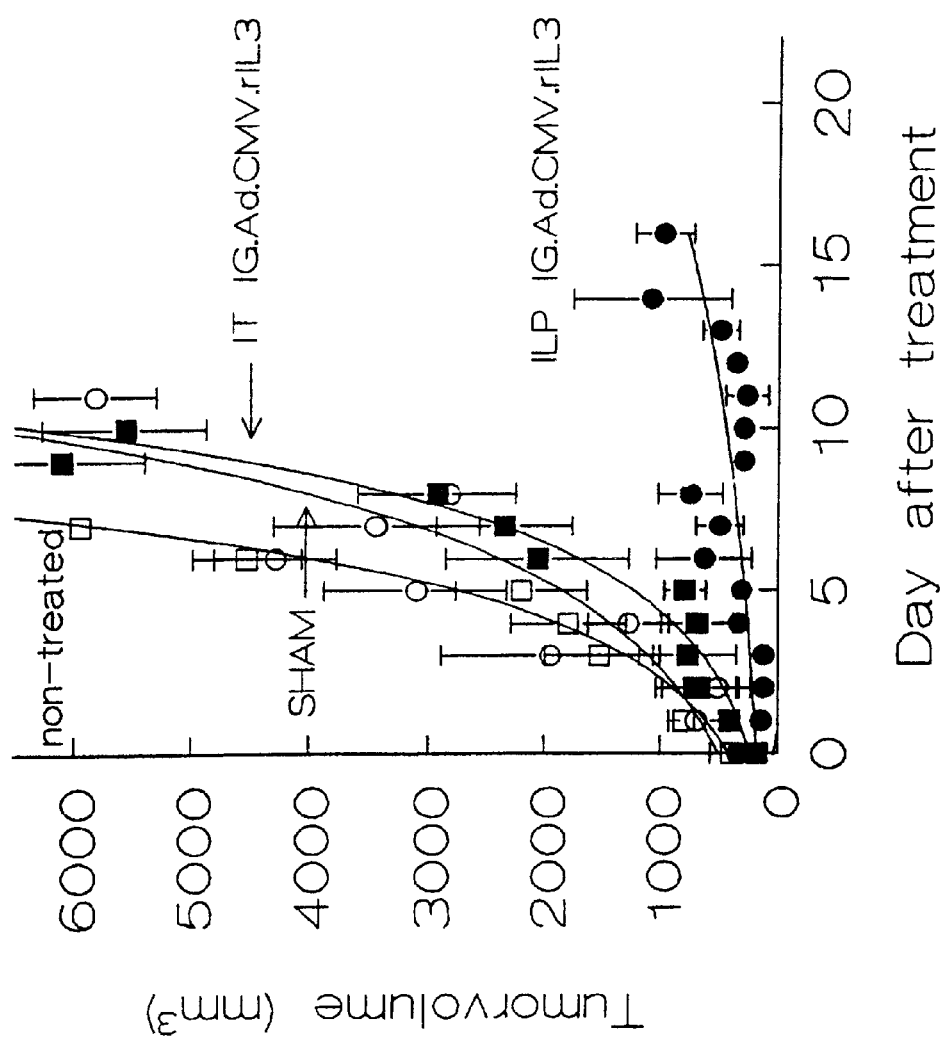

Rats bearing a BN175 tumor in their hindlimb (as described in example 3.1) were injected intra-tumorally (IT) with $1.10^9$ iu IG.Ad.CMV.rIL-3. An other group of rats bearing a BN175 tumor in their hindlimb underwent ILP for 15 minutes with $1.10^9$ iu IG.Ad.CMV.rIL-3 or perfusion buffer alone (the latter control perfusion is termed: sham ILP). The tumor sizes were followed in time. The results are depicted in FIG. 3.

Results and Conclusions

Delivery of rIL-3β (via an adenoviral vector results in a relative delay of the tumor growth of 15 days (determined for an arbitrary chosen tumor volume of 1000 mm³ and compared to the control sham ILP) in 8/9 of the treated BN175 tumors when the vector is delivered via ILP. One out of nine treated tumors shows no antitumor response (normal growth). Direct intratumoral injection of the IG.Ad.CMV.rIL-3β does not influence the tumor growth.

Example 7

Figure 4:
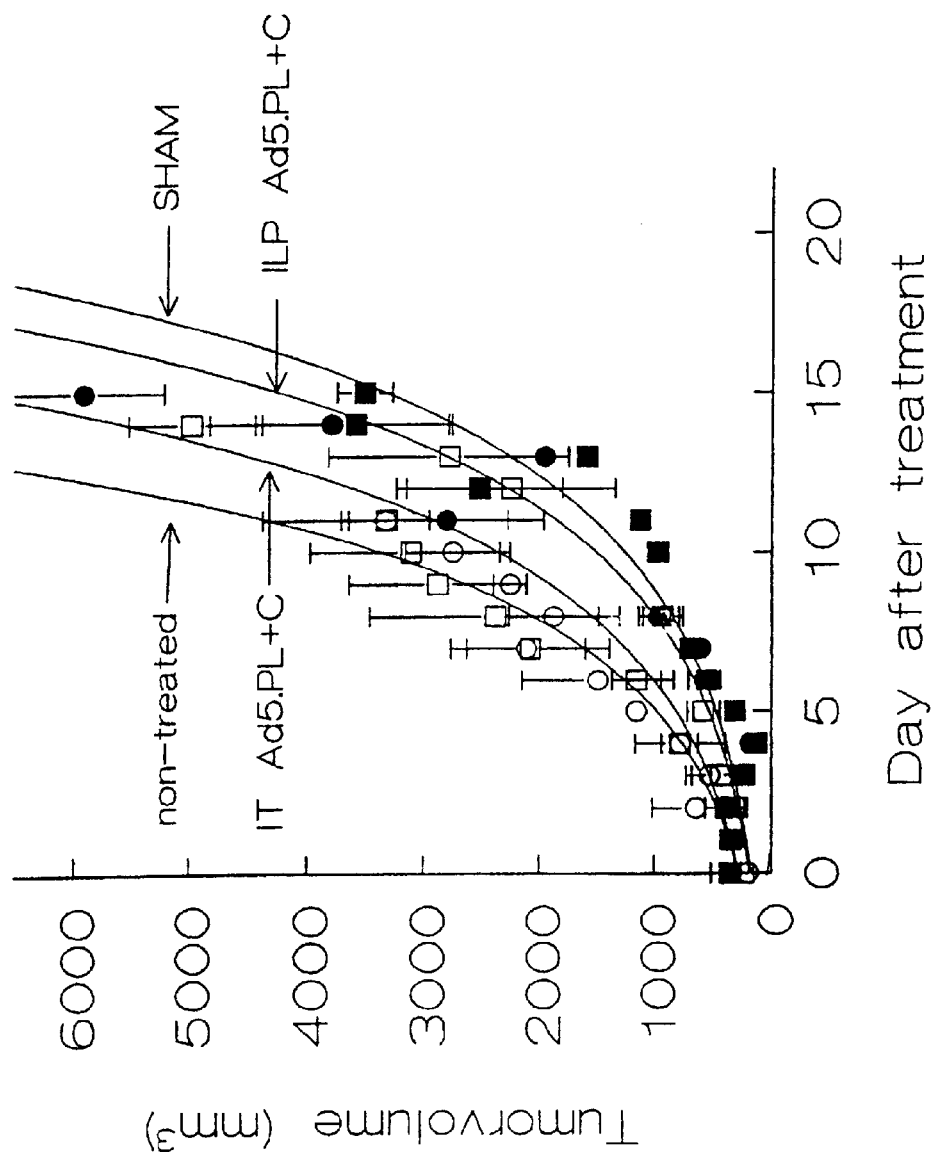

Effect of direct intra-tumoral injection or administration via the circulation (isolated limb perfusion) of ROS-1 osteosarcomas with an adenoviral vector carrying the interleukin-3 gene. ROS-1 tumor bearing rats (as described in example 3.1) were injected intra-tumorally (IT) with $1.10^9$ iu Ad5.PL+C. Ad5.PL+C is an adenovirus that is E1 deleted and has no tg containing adenoviral sequences and carries no gene (=an 'empty' control vector). An other group of rats underwent ILP for 15 minutes with $1.10^9$ iu Ad5.PL+C. The tumor sizes were followed in time. The results are depicted in FIG. 4.

Figure 5:
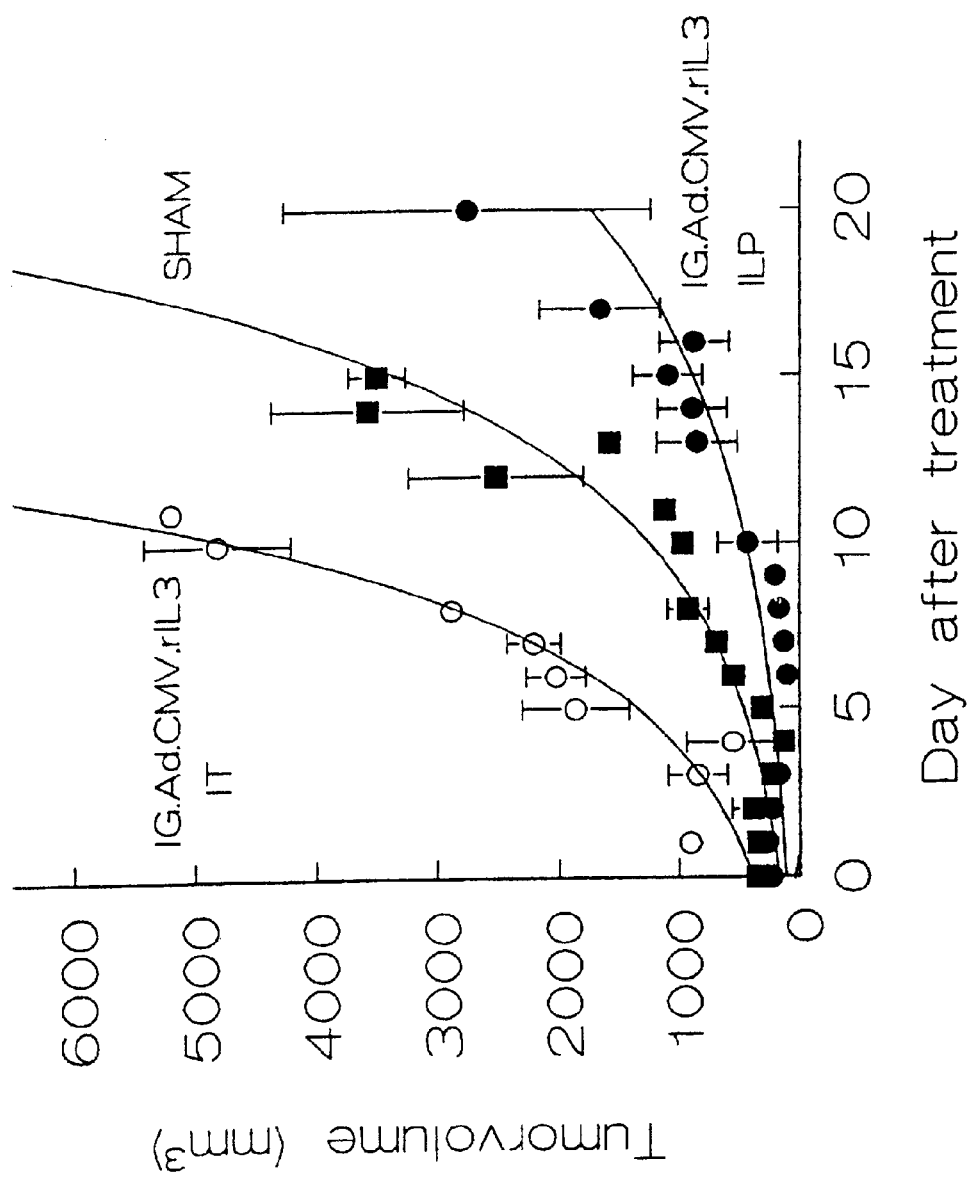

An other group of rats bearing a ROS-1 tumor in their hindlimb were injected intra-tumorally (IT) with $1.10^9$ iu IG.Ad.CMV.rIL-3. Other ROS-1 bearing rats underwent ILP for 15 minutes with $1.10^9$ iu IG.Ad.CMV.rIL-3 or perfusion buffer alone (the latter control perfusion is termed: sham ILP). The tumor sizes were followed in time. The results are depicted in FIG. 5.

Results and Conclusions

Delivery of IG.Ad.CMV.rIL-3 results in an antitumor effect (regression of the tumor growth) of all treated ROS-1 tumors when the adenovirus is delivered by ILP. Direct intra-tumoral injection with the same amount of IG.Ad.CMV.rIL-3 ($10^9$ iu) is not effective. The observed antitumor response is caused by the IL-3 gene and not by the adenovirus itself since the control virus Ad5.PL+C does not influence the tumor growth. A mock ILP without the addition of adenovirus or drug (termed sham ILP) delays the tumor growth compared to the non-treated tumors by 4 days (at the arbitrary chosen tumor volume of 2000 mm³). Compared to the sham ILP the ILP treatment with $10^9$ iu IG.Ad.CMV.rIL-3 results in a 9 days delay in tumor growth.

The observed delay in tumor growth after a sham ILP is explained by the washout of growth factor(s) or the need for oxygen for the growth of the ROS-1 tumor and is characteristic for ROS-1. In conclusion: Similar antitumor responses are observed after isolated limb perfusion with $1.10^9$ iu of IG.Ad.CMV.rIL-3 in two types of tumors.

Example 8

Antitumor effect of an adenoviral vector harboring the IL-3 gene driven by a weaker promoter, namely the MLP promoter.

Figure 6:
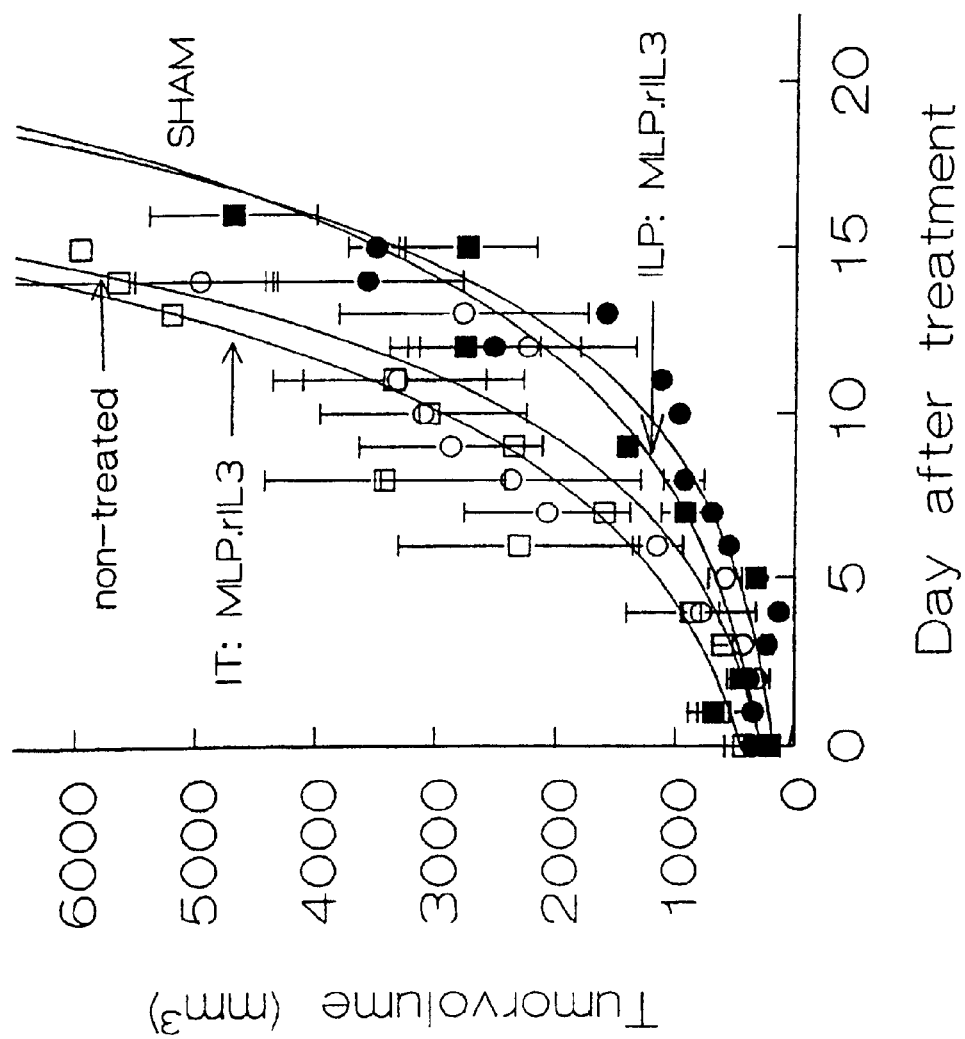

Rats bearing the ROS-1 tumor in their hindlimb (as described in example 3.1) were underwent ILP for 15 minutes with $1.0^9$ iu IG.Ad.MLP.rIL-3 (IG.Ad.MLP.rIL-3 is a similar adenovirus as IG.Ad.CMV.rIL-3 the only difference is the approximately 10-fold weaker MLP (major late promoter) promoter). An other group of rats bearing the ROS-1 tumor in their hindlimb were injected intra-tumorally with $1.10^9$ iu IG.Ad.MLP.rIL-3. The tumorsizes were followed in time. The results are depicted in FIG. 6.

Results and Conclusions

The results show that isolated limb perfusions or direct intratumoral injections of ROS-1 osteosarcoma with an adenoviral vector with the IL-3 gene driven by a (10-fold) weaker promoter (IG.Ad.MLP.rIL-3β) is not effective.

Example 9

Figure 7:
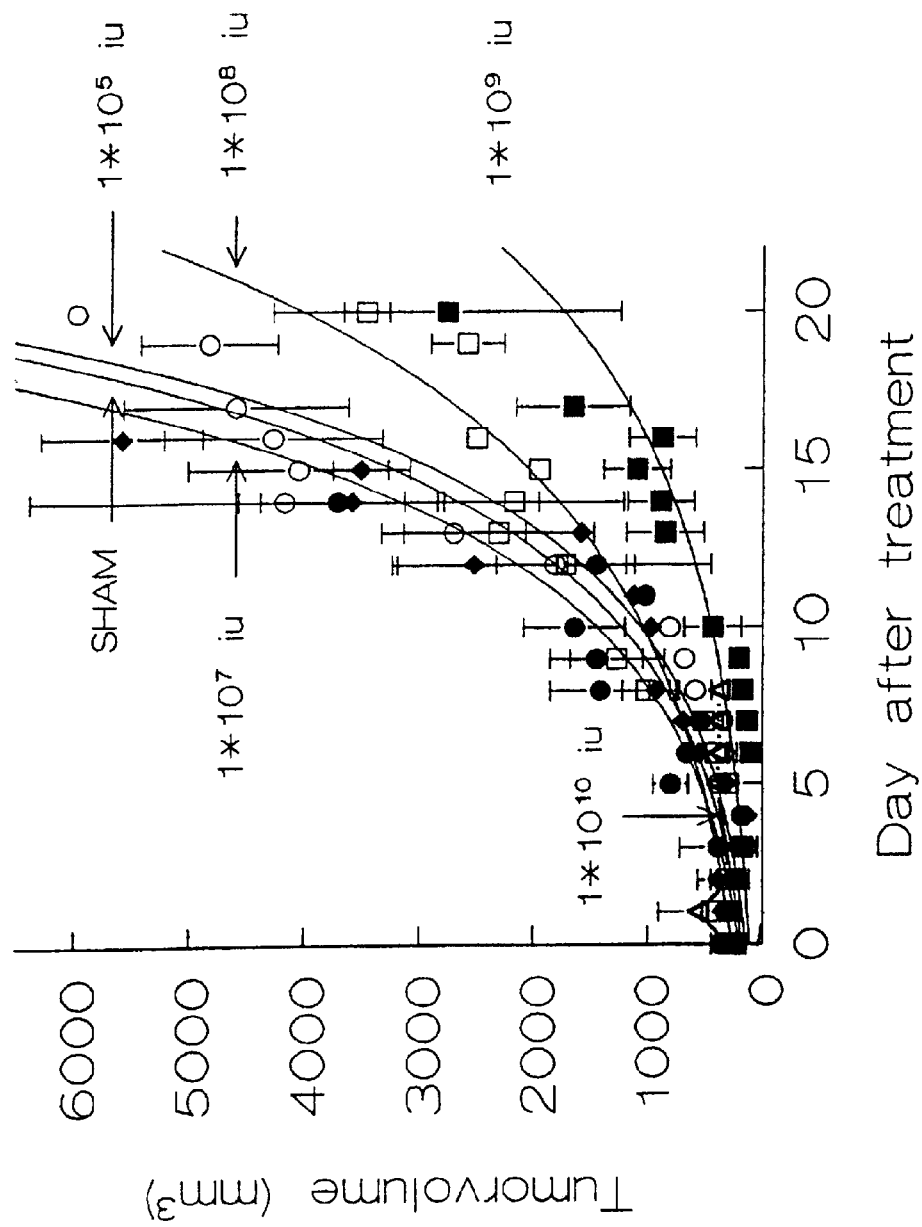

Antitumor effect of varying doses of an adenoviral vector carrying the interleukin-3 gene administered via the circulation (isolated limb perfusion). Rats bearing a ROS-1 tumor in their hindlimb (as described in example 3.1) underwent ILP with $1.10^5$ iu, $1.10^7$ iu, $1.10^8$ iu and $10^{10}$ iu of IG.Ad.CMV.rIL-3 for 15 minutes. The tumor sizes were followed in time. The results are depicted in FIG. 7.

Figure 8:
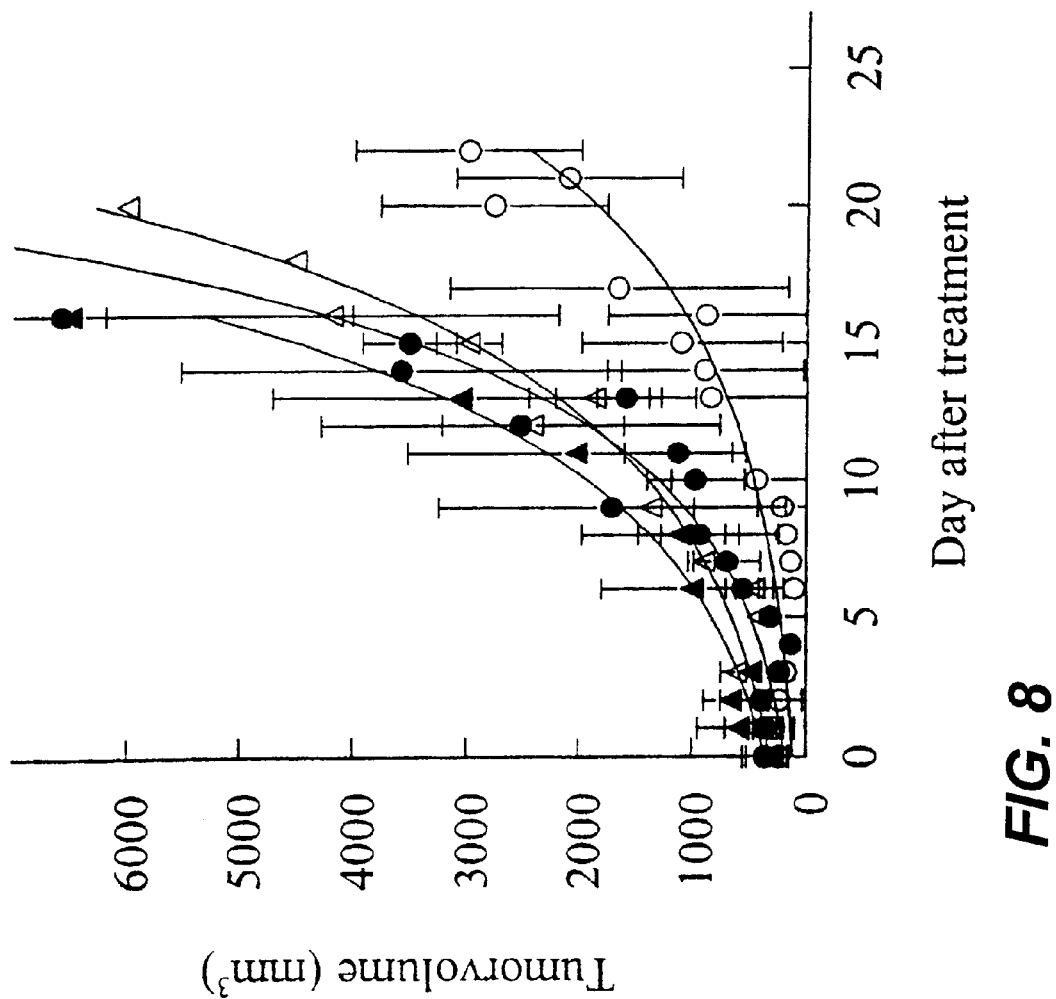

Another group of rats with BN175 sarcomas in their hindlimb (as described in chapter 3.1) underwent ILP for 15 minutes with $1.10^5$ iu and $1.10^7$ iu of IG.Ad.CMV.rIL-3. The tumor sizes were followed in time. The results are depicted in FIG. 8.

Figure 9:
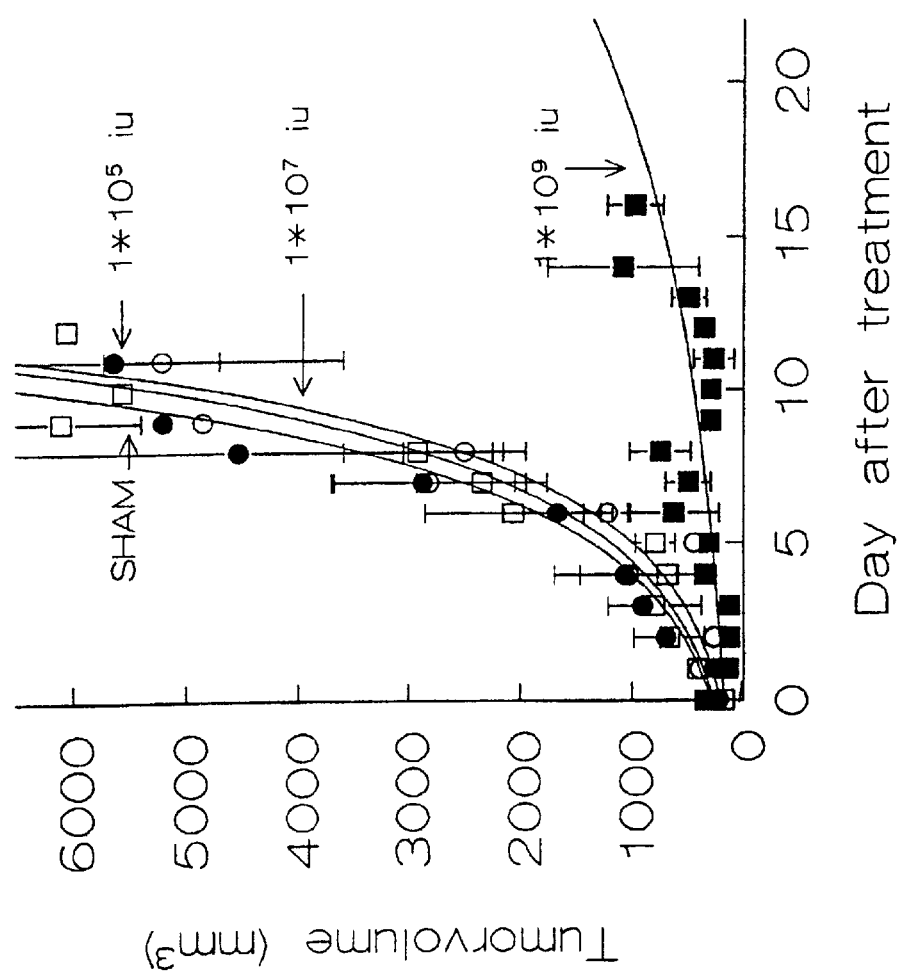

Other rats with ROS-1 tumors underwent ILP for 15 minutes with $2.10^8$ iu or $5.10^8$ iu of IG.Ad.CMV.rIL-3. The tumor sizes were followed in time. The results are depicted in FIG. 9.

Results and Conclusions

The results show that doses of $1.10^5$ iu or $1.10^7$ iu IG.Ad.CMV.rIL-3 result in no regression of the tumor growth after ILP both for ROS-1 and BN175 tumors. Isolated limb perfusions of ROS-1 tumors with $1.10^8$ iu of IG.Ad.CMV.rIL-3 show a small regression of the tumor growth. ILP of ROS-1 with $2.10^8$ iu and $5.10^8$ iu (performed with an other breed of rats, but with the same virus batch) did not show a regression of the tumor growth. Isolated limb perfusions of ROS-1 osteosarcomas with $1.10^{10}$ iu of IG.Ad.CMV.rIL-3 is lethal for the rats. At day 8 after treatment both rats were dead probably due to severe leucocytosis (leucocytes increased approx. 17-fold to $200–300.10^3$ leucocytes/mm³). At this dose an arrest in tumor growth is observed. In conclusion: the most optimal dose of IG.Ad.CMV.rIL-3 tested for isolated limb perfusion so far is $1.10^9$ iu.

Example 10

Figure 10:
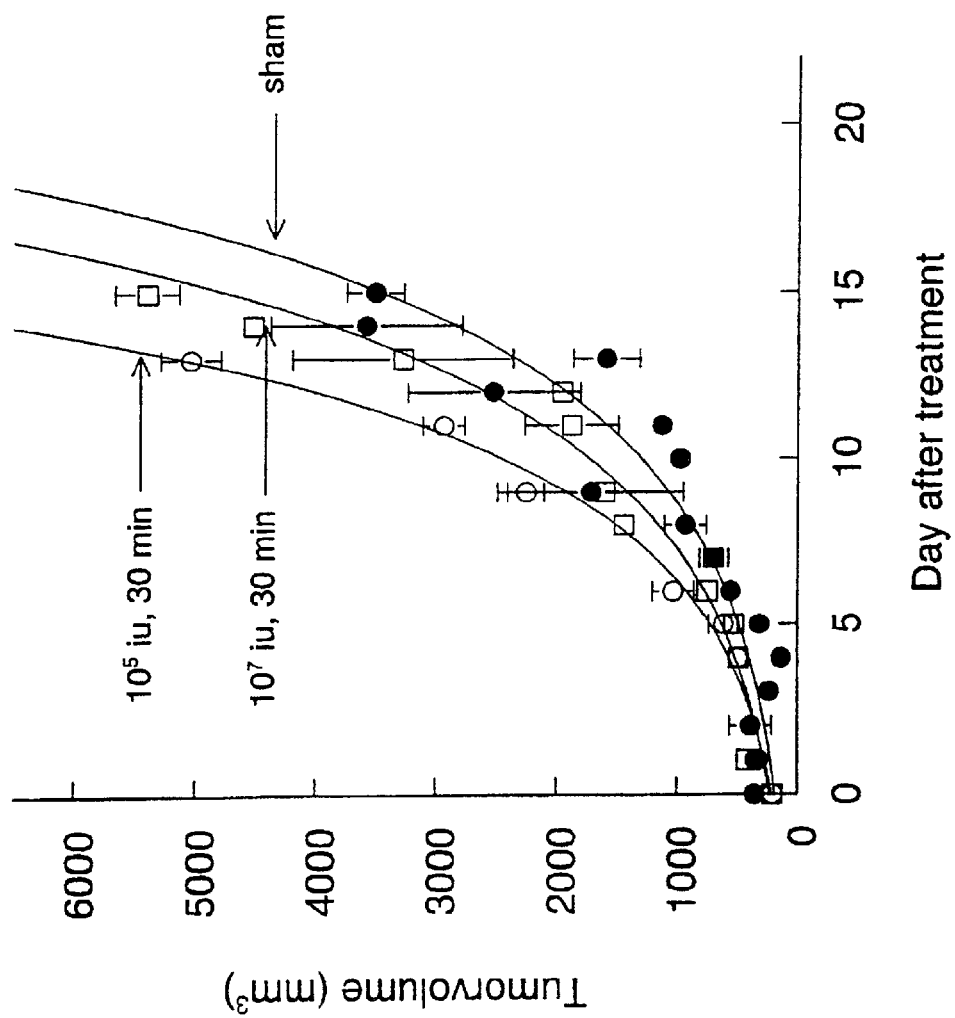

Antitumor effect of a 30 minutes isolated limb perfusions with a low dose of an adenoviral vector carrying the interleukin-3 gene. ROS-1 tumor bearing rats (as described in example 3.1) underwent ILP for 30 minutes with $1.10^7$ iu or $1.10^5$ iu of IG.Ad.CMV.rIL-3. The tumor sizes were followed in time. The results are depicted in FIG. 10.

Results and Conclusions

An increase of the perfusion time from 15 to 30 minutes does not result in a better antitumor effect when a dose of $1.10^5$ iu or $1.10^7$ iu IG.Ad.CMV.rIL-3 is used.

Example 11

Antitumor effect of administration via the circulation (isolated limb perfusion) of an adenoviral vector carrying the interleukin-3 gene and TNFα or melphalan.

Figure 11:
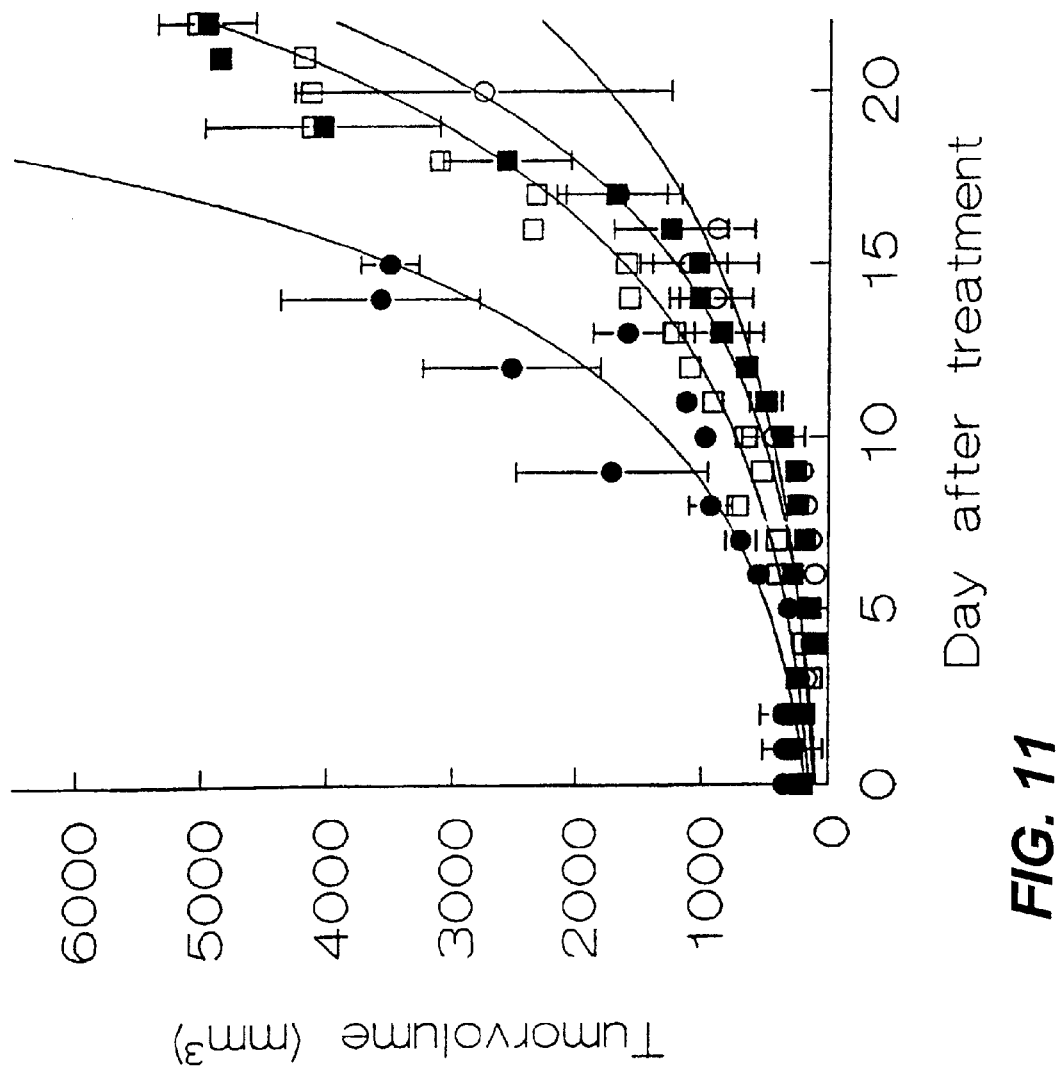

Rats bearing a ROS-1 osteosarcoma in their hindlimb (as described in example 3.1) underwent ILP with a mixture of a dose of $1.0^9$ iu IG.Ad.CMV.rIL-3 and a dose of 40 μg (=effective dose)of the cytostatic melphalan (Alkeran®, GlaxoWellcome, UK) per rat. The drug and recombinant adenoviral vector were added to the oxygenation chamber of the perfusion system immediately after each other. The tumor sizes were followed in time. An other group of rats were ILP treated with a total dose of 40 μg melphalan per rat. The results are depicted in FIG. 11.

Figure 12:
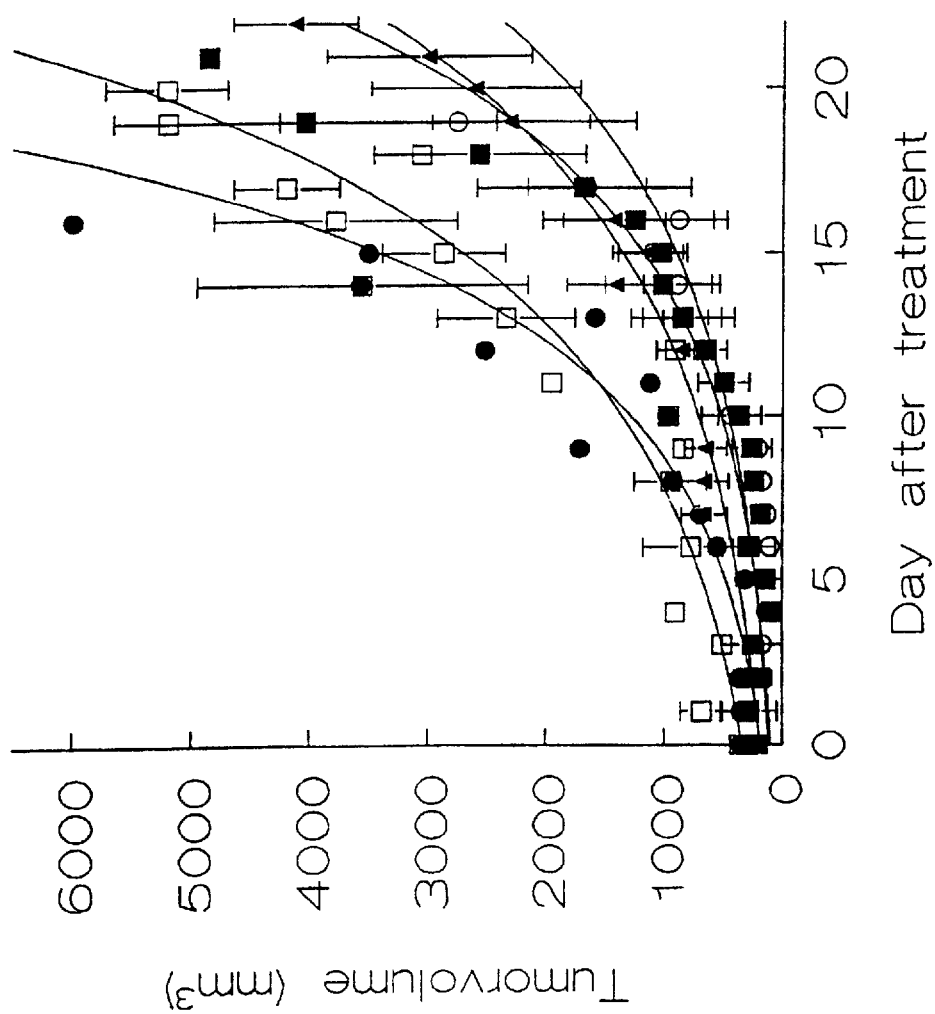

Other ROS-1 bearing rats underwent ILP with a mixture of a dose of $1.0^9$ iu IG.Ad.CMV.rIL-3 and a total dose of 50 μg TNFα (Boehringer Ingelheim, Germany) per rat or a dose of 50 μg TNFα alone (=the effective concentration). The tumor sizes were followed in time. An other group of rats were ILP treated with a mixture of a dose of 50 μg TNFα and a dose of 40 μg melphalan per animal. The tumor sizes were followed in time. The results are depicted in FIG. 12.

Figure 13:
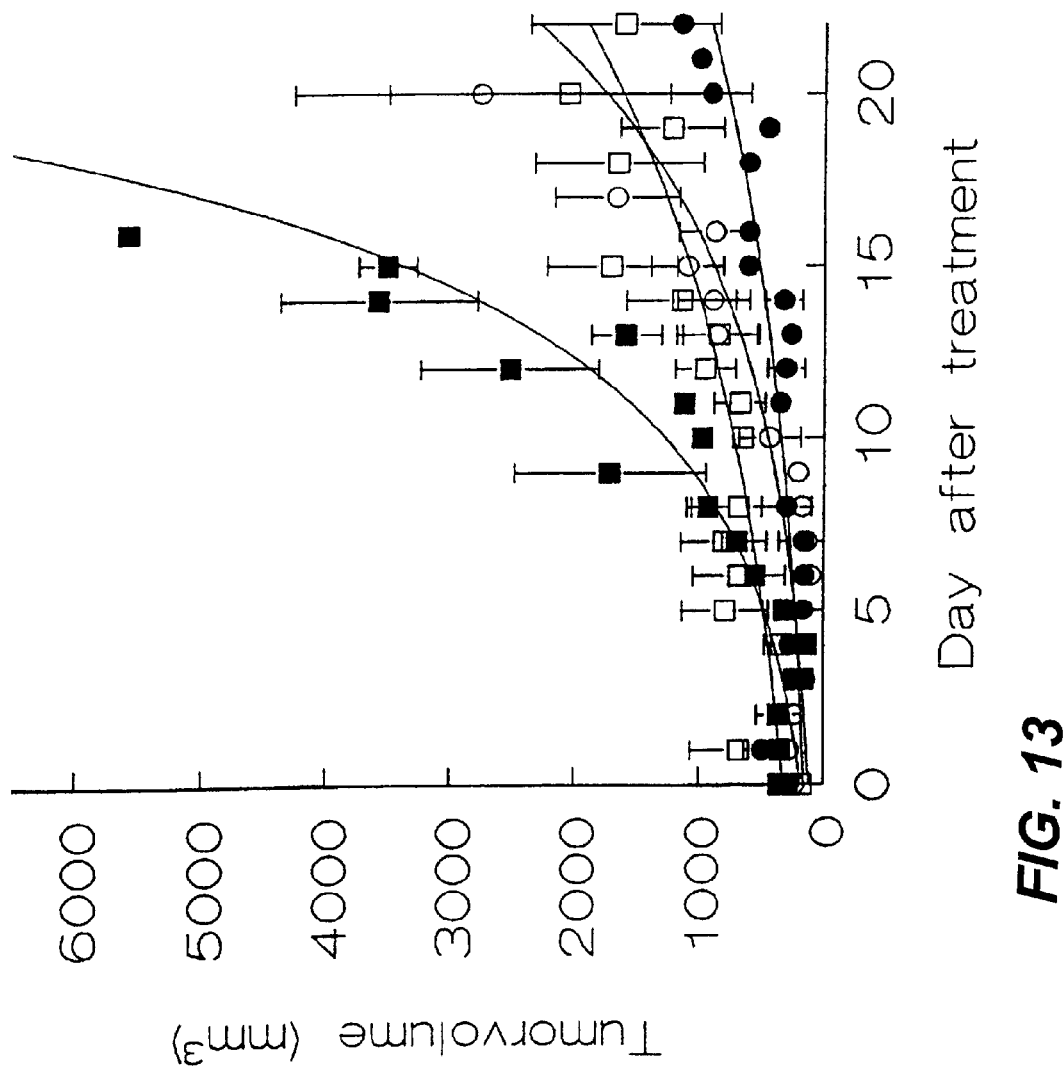

An other group of rats bearing a ROS-1 tumor in their hindleg underwent ILP with $1.10^9$ iu IG.Ad.CMV.rIL-3 and a dose of 200 μg doxorubicin (Adriblastina RTU, Farmitalia Carlo Erba) per rat. Rats underwent ILP with a dose of 200 μg doxorubicin per animal. The tumor sizes were followed in time. The results are depicted in FIG. 13.

Results and Conclusions

ILP with a monotherapy of $1.0^9$ iu IG.Ad.CMV.rIL-3 in the ROS-1 osteosarcoma model is at least as efficient as the established TNFα/melphalan combination therapy (similar antitumor effects). Addition of TNFα, melphalan or doxorubicin to the IG.Ad.CMV.rIL-3 perfusion does not influence the antitumor response. This indicates that there is no additional benefit or these established antitumor agents when used at their indicated effective concentrations.

Example 12

Effect of shorter perfusion times on the antitumor effect of an adenoviral vector carrying the interleukin-3 gene.

Figure 14:
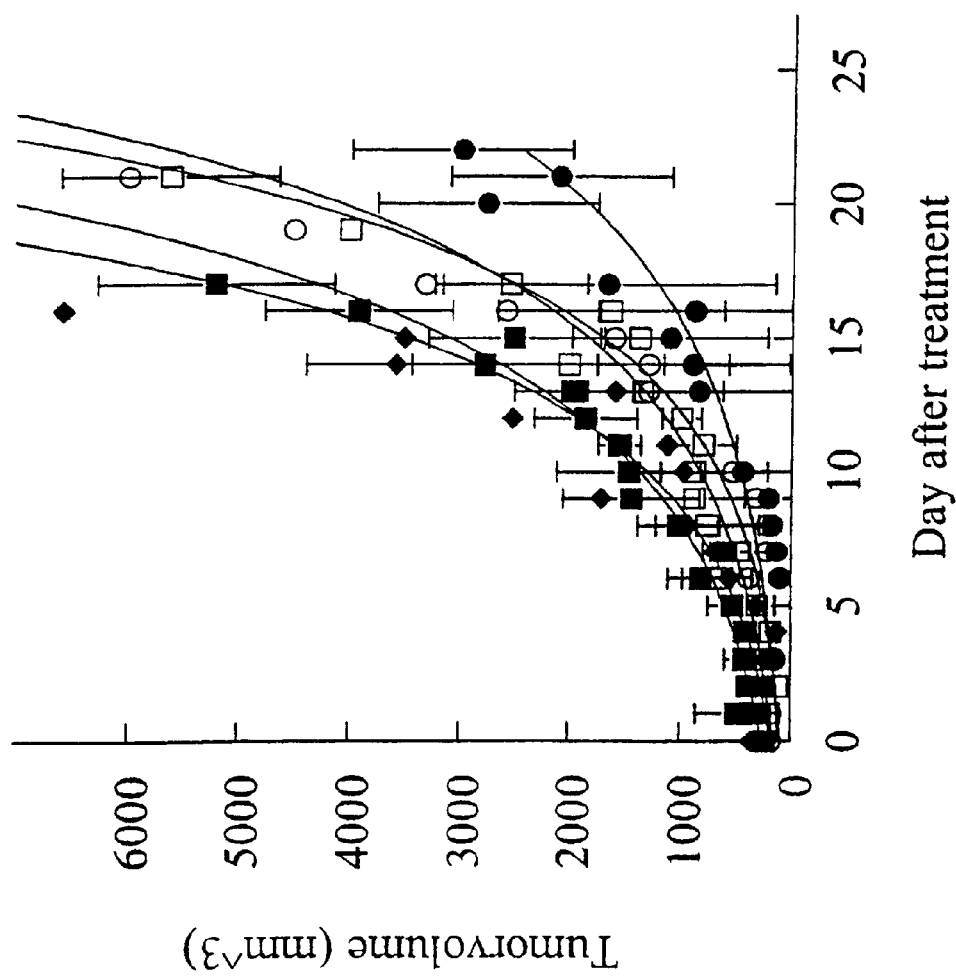

Rats bearing a ROS-1 osteosarcoma in their hindlimb (as described in example 3.1) underwent ILP (as described in example 3.2) with $1.0^9$ iu of IG.Ad.CMV.rIL-3 for 5 or 2 minutes. As a control a group of rats underwent ILP for 5 minutes with perfusion buffer alone (=sham ILP). The tumor sizes were followed in time. The results are depicted in FIG. 14.

Results and Conclusion

The results show that regression of the tumor growth comparable to a 15 minutes ILP is not observed when the perfusion time is reduced to 5 or 2 minutes.

Example 13

In vitro experiments with human cells with an adenoviral vector carrying the human interleukin-3 gene.

Human melanoma, sarcoma, Karposi sarcoma cells and human umbilical vein endothelial cells (HUVEC) are infected with an adenovirus with the human interleukin-3 gene (IG.Ad5.CLIP.hIL-3 (described in example 2)). The effect of adenoviral infection and hIL-3 protein expression is studied by the determination of the growth curve of the cells in the presence and absence of IG.Ad5.CLIP.hIL-3 for a period of 3–4 weeks after the infection. Other cultures of the above described cells are infected in a similar way. The protein production of the huIL-3 transgene is determined for 3 weeks by means of a huIL-3 ELISA (Quantikine,R&D systems) and a TF-1 cell activity assay.

Example 14

In vitro experiments with rat tumor cells with an adenoviral vector carrying the rat interleukin-3 gene.

Rat sarcoma (BN175) and osteosarcoma (ROS-1) cell lines are infected with an adenovirus with the rat interleukin-3 gene (IG.Ad.CMV.rIL-3 (described in example 1)). The effect of adenoviral infection and rIL-3 protein expression is studied by the determination of the growth curve of the cells in the presence and absence of IG.Ad.CMV.rIL-3 adenovirus for a period of 3–4 weeks. Other cultures of the same tumor cells are infected in a similar way. The protein production of the ratIL-3 transgene is determined for 3 weeks by means of an FDCP-1 cell activity assay.

Example 15

In vivo experiments with tumor bearing rats with an adenoviral vector carrying the human interleukin-3 gene. ROS-1 osteosarcoma bearing rats are treated via ILP (as described in chapter 3.2) for 15–30 minutes with $1.0^9$ iu of IG.Ad5.CLIP.hIL-3. Blood is sampled and tumor sizes are measured in time. The amount of huIL-3 in the rat blood is determined by means of a huIL-3 ELISA (Quantikine, R&D systems).

Example 16

Effect of administration via the circulation (isolated limb perfusion or intra-arterial infusion) of an adenoviral vector carrying the rat interleukin-3 gene with the liver excluded from the circulation.

16.1. Isolated Liver Perfusion Technique

Surgical procedures are performed under ether anaesthesia. For isolated liver perfusion the protocol as described in detail by Marinelli et al (1990) was used. Isolated liver perfusion (ILIP) involves complete vascular isolation of the liver during perfusion. For this a mid-line abdominal incision is made and two limbs of inflow were established by inserting cannulas into the pyloric branch of the portal vein and into the gastroduodenal branch of the common hepatic artery with their tips into the portal vein and the hepatic artery, respectively. The outflow limb is a cannula inserted into the caval vein. For a complete vascular isolation of the liver, all normal in- and outflow routes are clamped, the caval vein between liver and diaphragm and between cannula and the renal veins, the aorta proximal of the coeliac axis, the common hepatic artery and portal vein just proximal of the cannulas. The liver is perfused with the isotone perfusion fluid Haemmaccel (Behring Pharma, The Netherlands) for a time period of 10–45 minutes depending on the study protocol.

16.2. Experimental Set-up

Rats receive implants in their hindlimb with ROS-1 or BN175 tumors (as described in example 3.1). The liver is isolated from the blood circulation by means of an isolated liver perfusion as described in example 16.1. At the time the liver is excluded from the circulation the rats are intravenously or intra-arterially injected with $10^5$–$10^{10}$ iu of IG.Ad.CMV.rIL-3.

The isolated liver perfusion is performed for 10–45 minutes after which the blood circulation in the liver is restored. An other group of tumor bearing rats is intravenously or intra-arterially injected with $10^5$–$10^{10}$ iu of IG.Ad.CMV.rIL-3 without an isolated liver perfusion. The tumorsize development of the treated rats is followed in time. At the end organ pathology is performed.

Example 17

Effect of a longer perfusion time with $2.10^8$ iu on the antitumor effect of an adenoviral vector carrying the interleukin-3 gene.

ROS-1 osteosarcoma bearing rats are treated via ILP (as described in chapter 3.2) for 30 minutes with $2.10^8$ iu of IG.Ad5.CLIP.hIL-3. The antitumor effect is determined by daily tumorsize measurement.

Example 18

Effect of an intravenous or intra-arterial injection of $1.10^9$ iu of an adenoviral vector carrying the interleukin-3 gene on the organ pathology.

BN rats are injected intravenously or intra-arterially with $1.0^9$ iu IG.Ad.CMV.rIL-3. Health and behaviour of the animals is monitored daily. The organ pathology is studied at day 0,3,7,14,28 after injection.

Example 19

Phase I study synopsis in patients
2.1. Compound
IG.Ad5.CLIP.hIL-3
2.2. Study Title
Isolated limb perfusion (ILP) with an adenoviral vector containing the IL-3 gene in patients with extremity sarcoma or melanoma, a dose escalation study.
2.3. Development Phase
Phase I-II
2.4. Centers and Countries
NL, CH, Other TBD
2.5. Study Objectives
  Primary: determine the regional and the systemic tolerability of escalating doses up to $10^{11}$ particles of IG.Ad5.CLIP.hIL-3 administered in conjunction with ILP to patients with extremity melanoma or sarcoma, assessed by clinical and laboratory parameters.
  Secondary: determine the biological activity of IG.Ad5.CLIP.hIL-3 after ILP assessing clinical, radiological and laboratory parameters, determine pathological and clinical tumor response, assessed by histology and clinical parameters.
2.6. Design
  Prospective, open label, dose escalation, multicenter study.
2.7. Patients
  Key inclusion criteria: age 18–80 years, failure of standard treatment of sarcoma or melanoma, measurable disease, ability to give informed consent, any other anticancer therapy completed at least 4 weeks prior to study entry, fertile patients willing to practice contraception during 3 months following the gene therapy.
  Key exclusion criteria: any active or recent (within 7 days) infection, previous gene therapy of any kind, hematological disorder, autoimmune disease, plans for any additional anticancer therapy within 4 weeks after IG.Ad5.CLIP.hIL-3.
2.8. Sample Size
  Sequential cohorts of 3 patients will be entered at each of the planned dose levels. At the dose where >2/3 patients show a complete response (CR) or a partial response (PR) additional patients will be treated up to a total sample size of 24 of that level. If the MTD or the highest planned dose level is reached and <2/3 patients at a given dose level show a CR or PR, then additional patients, to a sample size of 5 will be treated at the MTD or the highest level. If >2/5 patients show CR or PR, the sample size is expanded to a total of 24 at that dose; if <2/5 show PR of CR, the study is closed.
2.9. Dose Level of IG.Ad5.CLIP.hIL-3
  $10^8$, $5 \times 10^8$, $10^9$, $5 \times 10^9$, $10^{10}$, $5 \times 10^{11}$ and $10^{11}$ vector particles added to the perfusate used for ILP and perfused for 90 minutes.
2.10. Dose Escalation Plan
  Dose escalation will proceed until $10^{11}$ particles; if however, at any dose level grade 3 or 4 (severe) systemic and/or >grade 4 local adverse events judged to be probably or definitely related to IG.Ad5.CLIP.hIL-3 occur in >2/3 patients in the 7 days following the ILP, then the MTD of IG.Ad5.CLIP.hIL-3 shall be defined as the dose below the one where these adverse events occurred.
2.11. Safety Criteria
  Physical examination, vital signs, laboratory evaluation, adverse events and concomitant medication usage will assess safety and tolerability. Regional toxicity in the affected limbs will be graded according to Wieberdink.
2.12. Efficacy Criteria
  Tumor response will be established at month 3 after the ILP. Complete response (CR) is defined as the disappearance of all evidence of disease with no new areas of diseases appearing within the perfusion field. Partial response (PR) is defined as a greater than 50% decrease in the sum of the perpendicular diameters of all measurable lesions with no single lesion increasing in the size and no new lesions appearing in the perfusion field. No change (NC) as regression of less than 50% of the sum of diameters or progression of less than 25% and progressive disease (PD) as greater than 25% increase of the sum of the diameters. Disease outside the perfused limb will also be measured and assessed according to standard WHO criteria.
2.13. Follow-up
  Patients will have regular clinical and laboratory examinations during 3 months following the gene therapy, will then be followed for survival only lifelong.

Legends to the figures

FIG. 1: Schematic presentation of the Ad5.pCLIP vector.

FIG. 2: Isolated limb perfusion or direct intra-tumoral injection with an adenoviral vector carrying the thymidine kinase gene, followed by treatment of ganciclovir.

Rats bearing a BN175 tumor in their hindlimb underwent ILP (●, n=5) or were directly injected intra-tumoral (○, n=9) with an adenoviral vector carrying the thymidine kinase gene.(TK), followed by treatment with gancyclovir (GCV). Sham ILP rats underwent a control ILP without adenovirus (■, n=2). Data represent the average±SEM. When the error bars are not visible, errors are within the symbol size.

FIG. 3: Isolated limb perfusion or direct intra-tumoral injection of BN175 sarcoma with an adenoviral vector carrying the interleukin-3 gene.

Rats bearing a BN175 tumor in their hindlimb underwent ILP (●, n=9) or were directly injected intra-tumoral (○, n=11) with an adenoviral vector carrying the interleukin-3 gene (IG.Ad.CMV.rIL-3β). Sham ILP rats underwent a control ILP without adenovirus (■, n=5). Non-treated BN175 bearing rats were not treated (□, n=4). Data represent the average ±SEM. When the error bars are not visible, errors are within the symbol size. Curves are fitted using an exponential model.

FIG. 4: Isolated limb perfusion or direct intra-tumoral injection of ROS-1 osteosarcoma with an adenoviral vector without a therapeutic gene.

Rats bearing a ROS-1 tumor in their hindlimb underwent ILP (●, n=4) or were directly injected intra-tumoral (○, n=4) with $1.10^9$ iu of a control adenoviral vector without a therapeutic gene (Ad5.PL+C). Sham ILP rats underwent a control ILP without adenovirus (■, n=6). Non-treated ROS-1 bearing rats were not treated (○, n=8). Data represent the average ±SEM. When the error bars are not visible, errors are within the symbol size. Curves are fitted using an exponential model.

FIG. 5: Isolated limb perfusion or direct intra-tumoral injection of ROS-1 osteosarcoma with an adenoviral vector carrying the interleukin-3 gene. Rats bearing a ROS-1 tumor in their hindlimb underwent ILP (●, n=9) or were directly injected intra-tumoral (○, n=6) with an adenoviral vector carrying the interleukin-3 gene (IG.Ad.CMV.rIL-3β). Sham ILP rats underwent a control ILP without adenovirus (■, n=6 (this curve represents the same group as described in FIG. 4)). Data represent the average±SEM. When the error bars are not visible, errors are within the symbol size. Curves are fitted using an exponential model.

FIG. 6: Isolated limb perfusion or direct intra-tumoral injection of ROS-1 osteosarcoma with an adenoviral vector carrying the interleukin-3 gene driven by a weaker promoter, namely the MLP promoter. Rats bearing a ROS-1 tumor in their hindlimb underwent ILP (■, n=4) or were directly injected intra-tumoral (○, n=4) with $1.10^9$ iu of an adenoviral vector carrying the interleukin-3 gene driven by the MLP promoter (IG.Ad.MLP. rIL-3β). Sham ILP rats underwent a control ILP without adenovirus (●, n=6) and non-treated rats were implanted with ROS-1 tumors but not treated (○, n=8) (the latter two curves represent the same group as described in FIG. 4). Data represent the average±SEM. When the error bars are not visible, errors are within the symbol size. Curves are fitted using an exponential model.

FIG. 7: Antitumor effect of varying doses of an adenoviral vector carrying the interleukin-3 gene administered via the circulation (isolated limb perfusion). Rats bearing a ROS-1 tumor in their hindlimb underwent ILP with $1.10^5$ iu (○, n=7), $1.10^7$ iu (●, n=6), $1.10^8$ iu (□, n=6) or $10^{10}$ iu(Δ, n=2) of IG.Ad.CMV.rIL-3. The sham ILP curve (♦, n=6) and the $1.10^9$ iu IG.Ad.CMV.rIL-3 ILP curve (■, n=9) are obtained from example 7 and are shown as reference curves. Data represent the Average ±SEM. When the error bars are not visible, errors are within the symbol size. Curves are fitted using an exponential model.

FIG. 8: Antitumor effect of doses below $1.10^9$ iu administered via the circulation (isolated limb perfusion) of an adenoviral vector carrying the interleukin-3 gene.

Rats bearing a BN175 tumor in their hindlimb underwent ILP with $1.10^5$ (●, n=5), $1.10^7$ iu (○, n=5) of an adenoviral vector carrying the interleukin-3. The sham ILP curve (□, n=6) and the $1.10^9$ iu IG.Ad.CMV.rIL-3 ILP curve (■, n=9) are obtained from example 7 and are shown as reference curves. Data represent the average ±SEM. When the error bars are not visible, errors are within the symbol size. Curves are fitted using an exponential model.

FIG. 9: Growth curves of ROS-1 tumors after isolated limb perfusions with $2.10^8$ iu and $5.10^8$ iu with an adenoviral vector carrying the interleukin-3 gene.

Rats bearing a ROS-1 tumor in their hindlimb underwent ILP for 15 minutes with $2.10^8$ iu (▲, n=5) or $5.10^8$ iu (Δ, n=4) IG.Ad.CMV.rIL-3. The 15 minutes sham ILP (●, n=6) and $1.10^9$ iu IG.Ad.CMV.rIL-3 (○, n=9) ILP curves are obtained from example 7 and shown as reference curves. Data represent the average±SEM. When the error bars are not visible, errors are within the symbol size. Curves are fitted using an exponential model.

FIG. 10: Growth curves of ROS-1 tumors after a 30 minutes isolated limb perfusion with $1.10^5$ iu or $1.10^7$ iu of an adenoviral vector carrying the interleukin-3 gene.

Rats bearing a ROS-1 tumor in their hindlimb underwent ILP for 30 minutes with 1.105 (○, n=2) or $1.10^7$ iu (□, n=2) of IG.Ad.CMV.rIL-3. The sham ILP curve (●, n=6) is obtained from example 7 and shown as reference curve. Data represent the average±STD. When the error bars are not visible, errors are within the symbol size. Curves are fitted using an exponential model.

FIG. 11: Growth curves of ROS-1 tumors after an isolated limb perfusion with an adenoviral vector carrying the interleukin-3 gene and the cytostatic melphalan.

Rats bearing a ROS-1 tumor in their hindlimb underwent ILP for 15 minutes with $1.0^9$ iu IG.Ad.CMV.rIL-3 in combination with 40 μg melphalan (■, n=5) or with 40 μg melphalan alone (□, n=5). The sham ILP (●, n=6) and $10^9$ iu IG.Ad.CMV.rIL-3 curves (○, n=9) are obtained from example 7 and shown as reference curve. Data represent the average ±STD. When the error bars are not visible, errors are within the symbol size. Curves are fitted using an exponential model.

FIG. 12: Growth curves of ROS-1 tumors after isolated limb perfusion with an adenoviral vector carrying the interleukin-3 gene and TNFα.

Rats bearing a ROS-1 tumor in their hindlimb underwent ILP for 15 minutes with $1.0^9$ iu IG.Ad.CMV.rIL-3 in combination with 50 μg TNFα (■, n=5), with 50 μg TNFα alone (□,n=4) or with 50 μg TNFα and 40 μg melphalan (▲, n=5). The sham ILP (●, n=6) and $10^9$ iu IG.Ad.CMV.rIL-3 curve (○, n=9) are obtained from example 7 and shown as reference curve. Data represent the average ±STD. When the error bars are not visible, errors are within the symbol size. Curves are fitted using an exponential model.

FIG. 13: Growth curves of ROS-1 tumors after an isolated limb perfusion with an adenoviral vector carrying the interleukin-3 gene and the cytostatic doxorubicin.

Rats bearing a ROS-1 tumor in their hindlimb underwent ILP for 15 minutes with $1.0^9$ iu IG.Ad.CMV.rIL-3 and 200 μg doxorubicin (●, n=4) or 200 μg doxorubicin alone (□, n=5). The sham ILP (■, n=6) and $1.0^9$ iu IG.Ad.CMV.rIL-3 (○, n=9)curves are obtained from example 7 and shown as reference curve. Data represent the average±STD. When the error bars are not visible, errors are within the symbol size. Curves are fitted using an exponential model.

FIG. 14: Growth curves of ROS-1 tumors after isolated limb perfusions for 2 or 5 minutes with an adenoviral vector carrying the interleukin-3 gene.

Rats bearing a ROS-1 tumor in their hindlimb underwent ILP for 2 minutes (○, n=1) or 5 minutes (□, n=6) with $1.10^9$ iu IG.Ad.CMV.rIL-3 or underwent a sham ILP for 5 minutes (■, n=6). The 15 minutes sham ILP (♦, n=6) and $1.0^9$ iu IG.Ad.CMV.rIL-3 (●, n=9) ILP curve is obtained from example 7 and shown as reference curves. Data represent the average±SEM. When the error bars are not visible, errors are within the symbol size. Curves are fitted using an exponential model.

Figure 15:
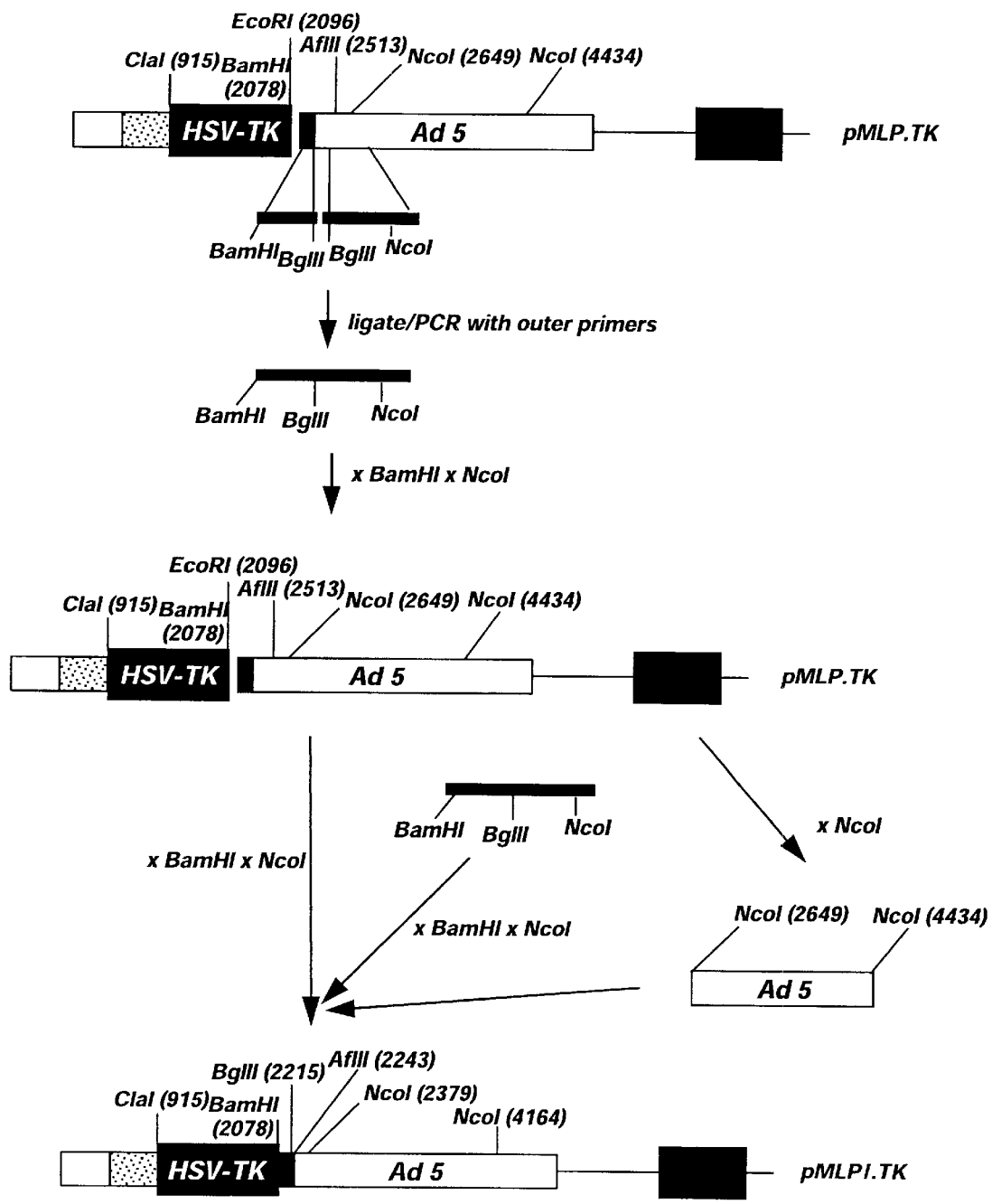

FIG. 15: Generation of PMLPI.TK.

Figure 16:
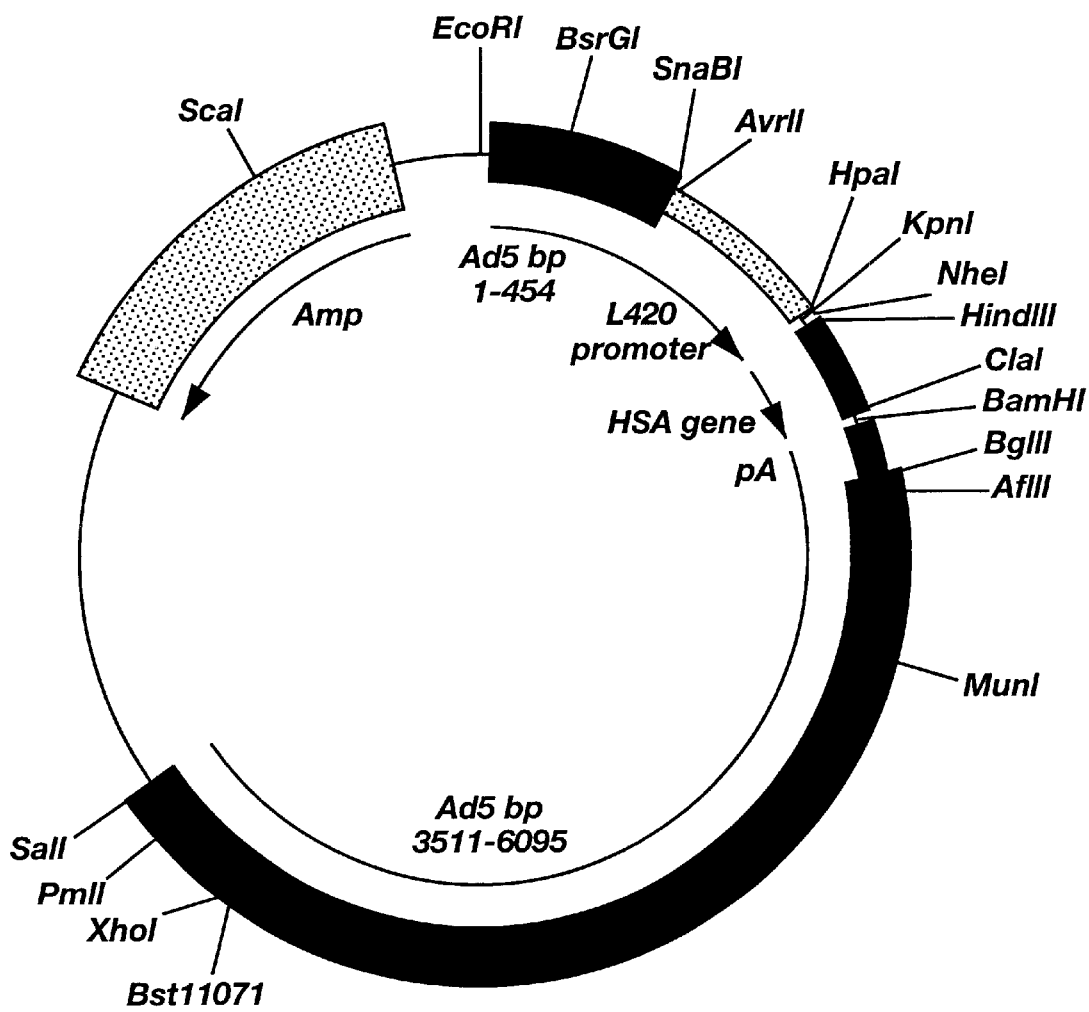

FIG. 16: Map of the adapter plasmid pAd5/L420-HSA.

FIG. 17: Results of the expression assay and biological activity assay of the hIL-3 transgene of the IG.AdS.CLIP.hIL-3 adenoviral vector.

FIG. 17A. hIL-3 ELISA: Since the $A_{450\,nm}$ is 0.541 it was concluded that the hIL-3 production was >2000 pg/ml (high production). hIL-3 transgene is produced.

FIG.17B: TF-1 bioactivity assay. TF-1 cells are for their growth dependent of the presence of hIL-3 in the culture medium. The less hIL-3 is present, the less well the cells grow. By a calorimetric assay with MTS/PMS (Promega) the proliferation can be monitored at A490 nm. A high proliferation (enough hIL-3) correlates with a high $A_{490\,nm}$. A dilution range of the samples are made to determine the hIL-3 presence.

The sample dilution table shows that the cells are proliferating (dilution 1: A 0.989) and that by dilution of the supernatant containing the hIL-3 protein the proliferation of the cells decreases. Functional hIL-3 is formed.

REFERENCES

1. Esandi, M. d. C., van Someren, G. G., Vincent, A. J. P. E., van Bekkum, D. W., Valerio, D., Bout, A., Noteboom, J. L. (1997). Treatment of malignant mesothelioma in an immunocompetent rat model using a recombinant adenovirus expressing the HSV-tk gene. Gene Therapy.4: 280–287.
2. Vincent, A. J. P. E., Esandi, M. d. C., van Someren, G. D., Noteboom, J. L., Vecht, C. J. J. C., Smitt, P. A. E. S., van Bekkum, D. W., Valerio, D., Hoogerbrugge, P. M., Bout, A. (1996a). Treatment of Leptomeningeal metastasis in a rat model using a recombinant adenovirus containing the HSV-tk gene. J.Neurosurgery. 85: 648–654.
3. Vincent, A. J. P. E., Vogels, R., van Someren, G., Esandi, M. d. C., Noteboom, J. L., Avezaat, C. J. J., Vecht, V. C., van Bekkum, D. W., Valerio, D., Bout, A., Hoogerbrugge, P. M. (1996b). Herpes Simplex Virus Thymidine kinase gene therapy for rat malignant braintumors. Human Gene Therapy. 7: 197–205.
4. Manusama, E. R., Nooijen, P. T. G. A., Stavast, J., Durante, N. M. C., Marquet, R. L., Eggermont, A. M. M. (1996). Synergistic antitumour effect of recombinant human tumour necrosis factor a with melphalan in isolated limb perfusion in the rat. British Journal of Surgery 83: 511–555.
5. Benckhuijsen, C., van Dijk, W. J., van 't Hoff, S. C. (1982). High-flow isolation perfusion of the rat hind limb in vivo. Journal of Surgical Oncology 21: 249–257.
6. Fortunati, E., Bout, A., Zanta, M. A., Valerio, D., Scarpa, M. (1996). In vitro and in vivo gene transfer to pulmonary cells mediated by cationic liposomes. Biochim.Biophys. Acta. in press.
7. Bout, A., Perricaudet, M., Baskin, G., Imler, J. L., Scholte, B. J., Pavirani, A., Valerio, D. (1994). Lung gene therapy: in vivo adenovirus mediated gene transfer to rhesus monkey airway epithelum. Human Gene Therapy.5: 3–10.
8. Barendsen, G W, Janse, H C. Differences in effectiveness of combined treatments with ionizing radiation and vinblastine, evaluation for experimental sarcomas and squamous cell carcinomas in rats. Int. J. Radiat. Oncol. Biol. Phys. (1987). 4: 95–102.
9. Marquet, R L, Schellekens, H, Westbroek, D L, Jeekel, J. Effect of treatment with interferon and cyclophosphamide on the growth of a spontaneous liposarcoma in rats. Int. J. Cancer. (1983). 31: 323–226.
10. Kort, W J, Zondervan, P E, Hulsman L O, Weijma, I M, Westbroek, D L. Incidence of spontaneous tumors in a group of retired breeder female brown norway rats. J. Natl. Cancer Inst. (1984). 72: 709–713.
11. Manusama, E R, Nooijen, P T G A, Stavast, J, Durante, N M C, Marquet, R L, Eggermont, A M M. Synergistic antitumour effect of recombinant human tumour necrosis faxtor α with melphalan in isolated limb perfusion in the rat. Br. J. Surg. (1996). 83: 551–555
12. Marinelli, A W K S, Van de Velde, C J H, Kuppen P J K, Franken, H C M, Souverij, J H M, Eggermont, A M M. A comparative study of isolated liver perfusion versus hepatic artery infusion with Mitomycin C in rats. Br. J. Cancer (1990) 62, 891–896.

What is claimed is:

1. A method of reducing tumor growth in at least one of sarcoma and osteosarcoma tumors in a subject, said method comprising administering to said subject by an Isolated Limb Perfusion technique a pharmaceutical composition comprising a recombinant adenoviral vector comprising a nucleic acid sequence encoding a protein having IL-3 activity.

2. The method according to claim 1 wherein a circulation isolated by the Isolated Limb Perfusion includes the tumor to be treated.

3. The method according to claim 1 wherein a circulation isolated by the Isolated Limb Perfusion excludes the tissue to be treated.

4. The method according to claim 1 wherein the recombinant adenoviral vector is provided in the form of a virus-like particle.

5. The method according to claim 4 wherein the virus-like particle encodes a human homolog of IL-3.

6. A kit of parts for the reduction in growth of sarcoma and osteosarcoma tumors, said kit comprising:
   a pharmaceutical composition comprising a recombinant adenoviral vector comprising nucleic acid encoding L-3 activity; and
   means for implementing Isolated Limb Perfusion.

7. The kit of parts of claim 6 wherein said recombinant adenoviral vector is present in the form of a virus-like particle.

8. The kit of parts of claim 7 wherein said virus-like particle is present in an amount of about $1 \times 10^6$ to $5 \times 10^9$ iu.

9. A method of genetically modifying at least one of sarcoma cells, osteosarcoma cells, and cells of the vasculature of sarcoma and osteosarcoma cells in a subject, whereby the genetically modified cells express IL-3 activity, the method comprising administering to the subject by Isolated Limb Perfusion a pharmaceutical composition comprising a recombinant adenoviral vector comprising a nucleic acid sequence encoding IL-3 activity.

10. The method according to claim 9 wherein a circulation isolated by the Isolated Limb Perfusion includes the cells to be genetically modified.

11. The method according to claim 9 wherein a circulation isolated by the Isolated Limb Perfusion excludes the cells to be genetically modified.

12. The method according to claim 9 wherein the recombinant adenoviral vector is provided in the form of a virus-like particle.

13. The method according to claim 12 wherein the virus-like particle is present in an amount of about $1 \times 10^6$ to $5 \times 10^9$ iu.

* * * * *

UNITED STATES PATENT AND TRADEMARK OFFICE
CERTIFICATE OF CORRECTION

PATENT NO. : 6,495,131 B1
DATED : December 17, 2002
INVENTOR(S) : Marie Elisabeth Draijer-van der Kaaden, Abraham Bout and Dirk Willem van Bekkum It is certified that error appears in the above-identified patent and that said Letters Patent is hereby corrected as shown below:

Column 7,
Line 23, change "$510^9$" to -- $5.10^9$ --

Column 14,
Line 51, change "PLTR10" to -- pLTR10 --

Column 15,
Line 11, change "PMLPI.TK" to -- pMLPI.TK- --

Column 18,
Line 45, change "L4cZ" to -- LacZ --

Column 21,
Lines 23, 37 and 52, change "$1.0^9$" to -- $1.10^9$ --

Column 22,
Line 31, change "$1.0^9$" to -- $1.10^9$ --

Column 25,
Line 13, change "(○, n=8)" to -- (□, n=8) --
Line 32, change "(○, n=4)" to -- (□, n=4) --
Line 50, change "Average" to -- average --

Column 26,
Line 11, change "1.105" to -- $1.10^5$ --
Lines 20, 44 and 57, change "$1.0^9$" to -- $1.10^9$ --
Line 67, change "IG.ADS.CLIP.hIL-3" to -- IG.AD5.CLIP.hIL-3 --

Column 27,
Line 7, change "calorimetric" to -- colorimetric --

UNITED STATES PATENT AND TRADEMARK OFFICE
CERTIFICATE OF CORRECTION

PATENT NO. : 6,495,131 B1
DATED : December 17, 2002
INVENTOR(S) : Marie Elisabeth Draijer-van der Kaaden, Abraham Bout and Dirk Willem van Bekkum It is certified that error appears in the above-identified patent and that said Letters Patent is hereby corrected as shown below:

<u>Column 31,</u>
Line 43, change "L-3" to -- IL-3 --

Signed and Sealed this

Twentieth Day of May, 2003

JAMES E. ROGAN
*Director of the United States Patent and Trademark Office*